(12) United States Patent
Attwood et al.

(10) Patent No.: US 6,372,883 B1
(45) Date of Patent: Apr. 16, 2002

(54) ANTIVIRAL MEDICAMENTS

(75) Inventors: Michael Richard Attwood, Hitchin; David Nigel Hurst, Welwyn; Philip Stephen Jones, Welwyn Garden; Paul Brittain Kay, Baldock; Tony Michael Raynham, Datchet; Francis Xavier Wilson, Welwyn Garden, all of (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/265,617

(22) Filed: Mar. 10, 1999

(30) Foreign Application Priority Data

Mar. 30, 1998 (GB) ............................................. 9806815

(51) Int. Cl.$^7$ ............................................. A61K 38/08
(52) U.S. Cl. ............................ 530/329; 530/330; 514/2; 514/17; 514/18; 424/189.1
(58) Field of Search ................. 514/2, 17, 18; 530/329, 330; 424/189.1

(56) References Cited

U.S. PATENT DOCUMENTS

| | | | |
|---|---|---|---|
| 5,866,684 A | | 2/1999 | Attwood et al. ............ 530/329 |
| 6,018,020 A | * | 1/2000 | Attwood et al. ............ 530/329 |
| 6,143,715 A | * | 1/2000 | Llinas-Brunet et al. ........ 514/2 |

FOREIGN PATENT DOCUMENTS

| WO | WO 98/17679 A1 | 4/1998 |
|---|---|---|
| WO | WO 98/22496 | 5/1998 |
| WO | WO 99/07734 A2 | 2/1999 |

OTHER PUBLICATIONS

R. Bartenschlager et al., Journal of Virology, vol. 67, No. 7, p. 3835–3844 (1993).
M.M. Bradford, Analytical Biochemistry, vol. 72, p. 248–254 (1976).
T.C.I. Wilkinson et al., Biochemical Society Transactions, vol. 25 S624 (1997).
Mori, E.A., "Biochemical and Biophysical Research Communications", vol. 231, (3) (Feb. 24, 1997) pp. 738–742.

* cited by examiner

*Primary Examiner*—Bennett Celsa
(74) *Attorney, Agent, or Firm*—George W. Johnston; Dennis P. Tramaloni

(57) ABSTRACT

The invention is concerned with amino acid derivatives of the formula

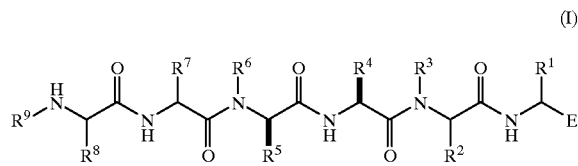

and salts of acidic compounds of formula I with bases, which are viral proteinase inhibitors useful as antiviral agents, especially for the treatment or prophylaxis of infections caused by Hepatitis C, Hepatitis G and human GB viruses.

15 Claims, No Drawings

ANTIVIRAL MEDICAMENTS

BACKGROUND OF THE INVENTION

The present invention is concerned with amino acid derivatives and a process for their manufacture. The invention is also concerned with pharmaceutical preparations containing these derivatives and with the use of these derivatives as medicaments, especially antiviral medicaments.

SUMMARY OF THE INVENTION

The antiviral medicaments provided in accordance with the present invention are amino acid derivatives represented by the general formula (I)

$$R^9\text{-N(H)-CH(R^8)-C(O)-N(H)-CH(R^7)-C(O)-N(R^6)-CH(R^5)-C(O)-N(H)-CH(R^4)-C(O)-N(R^3)-CH(R^2)-C(O)-N(H)-CH(R^1)-E}$$

wherein

E represents —CHO or —B(OH)$_2$;

$R^1$ represents lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl or lower alkynyl;

$R^2$ represents $R^{2a}$ or $R^{2b}$;

$R^{2a}$ represents lower alkyl, hydroxy-lower alkyl, carboxy-lower alkyl, aryl-lower alkyl, aminocarbonyl-lower alkyl or lower cycloalkyl-lower alkyl;

$R^{2b}$ represents aryl-lower alkoxy-aryl-lower alkyl or heteroaryl-lower alkyl;

$R^3$ represents hydrogen or lower alkyl; or $R^2$ and $R^3$ together represent di- or trimethylene optionally substituted by hydroxy;

$R^4$ represents lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;

$R^5$ represents $R^{5a}$ or $R^{5b}$;

$R^{5a}$ represents lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;

$R^{5b}$ represents lower cycloalkyl-lower alkyl;

$R^6$ represents hydrogen or lower alkyl;

$R^7$ represents $R^{7a}$ or $R^{7b}$;

$R^{7a}$ represents lower alkyl, hydroxy-lower alkyl, carboxy-lower alkyl, aryl-lower alkyl, lower cycloalkyl-lower alkyl or lower cycloalkyl;

$R^{7b}$ represents aryl-lower alkylthio-lower alkyl, aryl-lower alkoxy-aryl-lower alkyl, aryl-lower alkoxycarbonyl-lower alkyl, aryl-lower alkylcarbonyl-lower alkyl, nitroguanidino-lower alkyl, arylsulfonyl-guanidino-lower alkyl, lower alkylsulfonyl-lower alkyl, acetamidomethylthio-lower alkyl, aryl or heteroaryl-lower alkyl;

$R^8$ represents $R^{8a}$ or $R^{8b}$;

$R^{8a}$ represents lower alkyl, hydroxy-lower alkyl, carboxy-lower alkyl or aryl-lower alkyl;

$R^{8b}$ represents mercapto-lower alkyl, lower alkylsulfonyl-lower alkyl, aryl-lower alkoxy-lower alkyl or aryl-heteroaryl-lower alkyl;

$R^9$ represents $R^{9a}$ or $R^{9b}$;

$R^{9a}$ represents lower alkylcarbonyl, carboxy-lower alkylcarbonyl, arylcarbonyl, lower alkylsulfonyl, arylsulfonyl, lower alkoxycarbonyl or aryl-lower alkoxycarbonyl; and $R^{9b}$ represents aryl-lower alkylcarbonyl, heteroaryl-lower alkylcarbonyl, arylaminocarbonyl-lower alkylcarbonyl, heteroarylthio-lower alkylcarbonyl, heteroarylcarbonyl, hydroxyfluorenylcarbonyl, heteroarylcarbonyl-lower alkylcarbonyl, lower alkoxy-lower alkylcarbonyl, arylcarbonyl-lower alkylcarbonyl, lower alkoxy-lower alkoxy-lower alkoxy-lower alkylcarbonyl, arylcarbonylamino-lower alkylcarbonyl, lower cycloalkyl-lower alkylcarbonyl, lower alkylcarbonyl-lower cycloalkyl-lower alkylcarbonyl, lower alkylcarbonylamino-lower alkylcarbonyl, heterocyclylcarbonyl, lower alkylcarbonyloxy-lower alkylcarbonyl, lower alkoxycarbonyl-lower alkylcarbonyl, aryloxy-lower alkylcarbonyl, lower alkynylcarbonyl or lower cycloalkylcarbonyl;

provided that $R^2$, $R^5$, $R^7$, $R^8$ and $R^9$ do not simultaneously represent $R^{2a}$, $R^{5a}$, $R^{7a}$, $R^{8a}$ and $R^{9a}$, respectively;

and salts of acidic compounds of formula I with bases. The compounds of formula I inhibit proteinases of viral origin and can be used in the treatment of viral infections, especially viral infections caused by hepatitis C, hepatitis G and human GB viruses.

DETAILED DESCRIPTION OF THE INVENTION

The antiviral medicaments provided in accordance with the present invention are amino acid derivatives represented by the general formula (I)

$$R^9\text{-N(H)-CH(R^8)-C(O)-N(H)-CH(R^7)-C(O)-N(R^6)-CH(R^5)-C(O)-N(H)-CH(R^4)-C(O)-N(R^3)-CH(R^2)-C(O)-N(H)-CH(R^1)-E}$$

wherein

E represents —CHO or —B(OH)$_2$;

$R^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

$R^2$ represents $R^{2a}$ or $R^{2b}$;

$R^{2a}$ is selected from the group consisting of lower alkyl, hydroxy-lower alkyl, carboxy-lower alkyl, aryl-lower alkyl, aminocarbonyl-lower alkyl and lower cycloalkyl-lower alkyl;

$R^{2b}$ represents aryl-lower alkoxy-aryl-lower alkyl or heteroaryl-lower alkyl;

$R^3$ represents hydrogen or lower alkyl; or $R^2$ and $R^3$ together represent di-or trimethylene optionally substituted by hydroxy;

$R^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

$R^5$ represents $R^{5a}$ or $R^{5b}$;

$R^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

$R^{5b}$ represents lower cycloalkyl-lower alkyl;

$R^6$ represents hydrogen or lower alkyl;

$R^7$ represents $R^{7a}$ or $R^{7b}$;

$R^{7a}$ is selected from the group consisting of lower alkyl, hydroxy-lower alkyl, carboxy-lower alkyl, aryl-lower alkyl, lower cycloalkyl-lower alkyl and lower cycloalkyl;

$R^{7b}$ is selected from the group consisting of aryl-lower alkylthio-lower alkyl, aryl-lower alkoxy-aryl-lower alkyl, aryl-lower alkoxycarbonyl-lower alkyl, aryl-lower alkylcarbonyl-lower alkyl, nitroguanidino-lower alkyl, arylsulfonyl-guanidino-lower alkyl, lower alkylsulfonyl-lower alkyl, acetamidomethylthio-lower alkyl, aryl and heteroaryl-lower alkyl;

$R^8$ represents $R^{8a}$ or $R^{8b}$;

$R^{8a}$ is selected from the group consisting of lower alkyl, hydroxy-lower alkyl, carboxy-lower alkyl and aryl-lower alkyl;

$R^{8b}$ is selected from the group consisting of mercapto-lower alkyl, lower alkylsulfonyl-lower alkyl, aryl-lower alkoxy-lower alkyl and aryl-heteroaryl-lower alkyl;

$R^9$ represents $R^{9a}$ or $R^{9b}$;

$R^{9a}$ is selected from the group consisting of lower alkylcarbonyl, carboxy-lower alkyl-carbonyl, arylcarbonyl, lower alkylsulfonyl, arylsulfonyl, lower alkoxycarbonyl and aryl-lower alkoxycarbonyl; and $R^{9b}$ is selected from the group consisting of aryl-lower alkylcarbonyl, heteroaryl-lower alkylcarbonyl, arylaminocarbonyl-lower alkylcarbonyl, heteroarylthio-lower alkylcarbonyl, heteroarylcarbonyl, hydroxyfluorenylcarbonyl, heteroarylcarbonyl-lower alkylcarbonyl, lower alkoxy-lower alkylcarbonyl, arylcarbonyl-lower alkylcarbonyl, lower alkoxy-lower alkoxy-lower alkoxy-lower alkylcarbonyl, arylcarbonylamino-lower alkylcarbonyl, lower cycloalkyl-lower alkylcarbonyl, lower alkylcarbonyl-lower cycloalkyl-lower alkylcarbonyl, lower alkylcarbonylamino-lower alkylcarbonyl, heterocyclylcarbonyl, lower alkylcarbonyloxy-lower alkylcarbonyl, lower alkoxycarbonyl-lower alkylcarbonyl, aryloxy-lower alkyl-carbonyl, lower alkynylcarbonyl and lower cycloalkylcarbonyl;

with the proviso that $R^2$, $R^5$, $R^7$, $R^8$ and $R^9$ do not simultaneously represent $R^{2a}$, $R^{5a}$, $R^{7a}$, $R^{8a}$ and $R^{9a}$, respectively; and salts of acidic compounds of formula I with bases.

As used herein, the term "lower alkyl" denotes a straight-chain or branched-chain alkyl group containing 1–7, e.g. methyl, ethyl, propyl, isopropyl, n-butyl, isobutyl, sec.butyl, tert.butyl, n-pentyl, neopentyl, preferably 1–4, carbon atoms, and the like. The term "lower alkenyl" denotes a straight-chain or branched-chain alkenyl group containing 2–7 carbon atoms, e.g. vinyl, allyl, n-propenyl, n-butenyl and the like, and the term "lower alkynyl" denotes a straight-chain or branched-chain alkynyl group containing 2–7 carbon atoms, e.g. propargyl, 5-hexynyl,6-heptynyl and the like. The term "cycloalkyl" denotes a cycloalkyl group containing 3–7 carbon atoms, i.e. cyclopropyl, cyclobutyl, cyclopentyl, cyclohexyl and cycloheptyl. The term "lower alkoxy" denotes a lower alkyl group as defined hereinbefore, which is bonded via an oxygen atom, e.g. methoxy, ethoxy, n-propoxy, isopropoxy, n-butoxy, isobutoxy, tert.butoxy and the like. The term "aryl" denotes a monocyclic or polycyclic aromatic group, e.g. phenyl, naphthyl or the like, which may be unsubstituted or substituted by one or more substituents selected from e.g. lower alkyl, lower alkoxy, halo, i.e. fluoro, chloro, bromo or iodo, halo-lower alkyl, e.g. trifluoromethyl, hydroxy, sulfamoyl and acetamido. The term "heteroaryl" denotes a 5- or 6-membered aromatic heterocyclic group which contains N, O or S as the hetero atom(s) and which is optionally fused with benzene or optionally substituted in the same manner as the aryl group defined hereinbefore. Furyl, thienyl, pyridyl, pyrimidinyl, benzofuranyl, benzothienyl, quinolyl, isoquinolyl, indolyl and the like are examples of heteroaryl groups. The term "heterocyclyl" denotes a saturated or partly unsaturated, 5- or 6-membered heterocyclic group which contains N, O or S as the hetero atom(s) and which is optionally fused with benzene or optionally substituted in the same manner as the aryl group defined hereinbefore or by oxo or thioxo. Examples of heterocyclyl groups are thiazolidinyl, 1,2,3,4-tetrahydropyrimidinyl, hexahydropyrimidinyl, 5,6-dihydropyranyl and the like. It will be appreciated that the aforementioned definitions apply to the respective groups when they stand alone or are combined with a further group or groups.

The following sub-groups of compounds of those represented by formula I are preferred:

(IA)

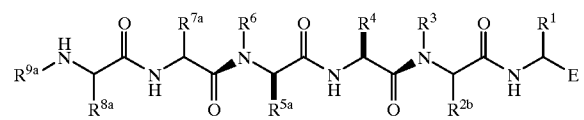

(IB)

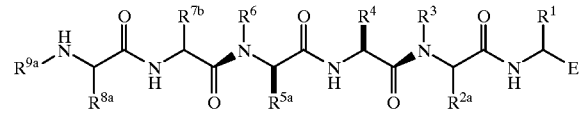

(IC)

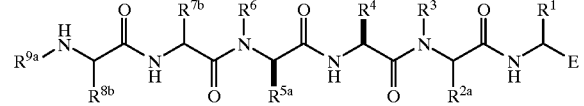

(ID)

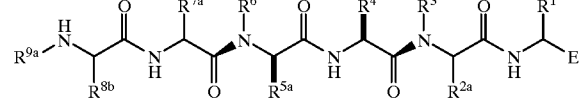

(IE)

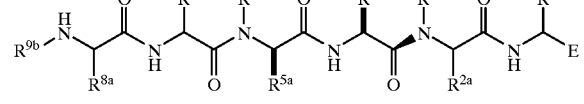

(IF)

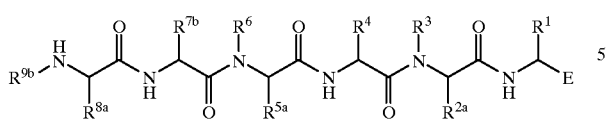

wherein E, $R^1$, $R^{2a}$, $2b$, $R^3$, $R^4$, $R^{5a}$, $R^6$, $R^{7a}$, $R^{7b}$, $R^{8a}$, $R^{8b}$, $R^{9a}$ and $R^{9b}$ have the significance given earlier.

In formulae I and IA to IF $R^1$ preferably represents lower alkyl or halo-lower alkyl, especially fluoro-lower alkyl. $R^{2a}$ preferably represents lower alkyl. $R^3$ preferably represents hydrogen. $R^4$ preferably represents lower alkyl. $R^{5a}$ preferably represents aryl-lower alkyl. $R^6$ preferably represents hydrogen. $R^{7a}$ preferably is a member of the group consisting of lower alkyl, carboxy-lower alkyl, aryl-lower alkyl, lower cycloalkyl-lower alkyl and lower cycloalkyl. $R^{7b}$ preferably preferably is a member of the group consisting of nitroguanidino-lower alkyl, acetamidomethylthio-lower alkyl and lower alkylsulfonyl-lower alkyl. $R^{8a}$ preferably is a member of the group consisting of carboxy-lower alkyl, hydroxy-lower alkyl and aryl-lower alkyl. $R^{8b}$ preferably represents aryl-heteroaryl-lower alkyl. $R^{9a}$ preferably is a member of the group consisting of lower alkylcarbonyl, carboxy-lower alkylcarbonyl and arylcarbonyl. $R^{9b}$ preferably preferably is a member of the group consisting of heteroarylcarbonyl, hydroxyfluorenylcarbonyl, heterocyclylcarbonyl, heteroarylcarbonyl-lower alkylcarbonyl, heteroaryl-lower alkylcarbonyl and aryl-lower alkylcarbonyl.

Examples of preferred compounds falling within formulae IA to IF are:

Formula IA:

2(RS)-[[N-[N-[N-[N-[N-(3-Carboxypropionyl)-L-α-aspartyl]-L-α-glutamyl]-2-methyl-L-phenylalanyl]-3-methyl-L-valyl]-O-benzyl-L-tyrosyl]amino]-4,4,4-trifluorobutyraldehyde;

2(RS)-[[N-[N-[N-[N-[N-(3-carboxypropionyl)-L-α-aspartyl]-L-α-glutamyl]-2-methyl-L-phenylalanyl]-3-methyl-L-valyl]-O-(2,6-dichlorobenzyl)-L-tyrosyl]amino]-4,4,4-trifluorobutyraldehyde; and 2(RS)-[[N-[N-[N-[N-[N-(3-carboxypropionyl)-L-α-aspartyl]-L-α-glutamyl]-2-methyl-L-phenylalanyl]-3-methyl-L-valyl]-2-(3-thienyl)-L-alanyl]amino]-4,4,4-trifluorobutyraldehyde.

Formula IB:

2(RS)-[[N-[N-[N-[N-[N-(3-Carboxypropionyl)-L-α-aspartyl]-O-benzyl-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-N6-nitro-L-arginyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-S-(acetamidomethyl)-L-cysteinyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-S-benzyl-L-cysteinyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-3-(3-thenyl)-D-alanyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-D-tryptophyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-O-benzyl-D-tyrosyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-S-(4-methoxybenzyl)-D-cysteinyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-O-benzyl-D-threonyl]-2-methyl-L-phenylalanyl]-3-methyl-L-valyl]-L-leucyl]amino]-4,4,4-trifluorobutyraldehyde;

2(RS)-[[N-[N-[N-[N-(4-chloro-3-sulphamoylbenzoyl)-L-seryl)]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(4-acetamidobenzoyl)-L-seryl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-(3-hydroxy-4,5-dimethoxybenzoyl)-L-seryl)]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(2-ethylbutyryl)-L-seryl)]-O-benzyl-D-seryl]-2-methyl-L-phenylalanyl]-3-methyl-L-valyl]-L-leucyl]amino]-4,4,4-trifluorobutyraldehyde;

1(RS)-[[N-[N-[N-[N-(N-acetyl-L-α-aspartyl)-S,S-dioxo-L-methionyl]-2-methyl-L-phenylalanyl]-3-methyl-L-valyl]-L-leucyl]amino]propylboronic acid (SEQ ID NO:3); and 1(RS)-[[N-[N-[N-[N-(N-acetyl-L-α-aspartyl)-S-[(acetamido)methyl]-L-cysteinyl]-2-methyl-L-phenylalanyl]-3-methyl-L-valyl]-L-leucyl]amino]-propylboronic acid (SEQ ID NO. 4).

Formula IC:

1(RS)-[[N-[N-[N-[N-[N-Acetyl-1-(2,4-dinitrophenyl)-L-histidyl]-O-benzyl-L-α-glutamyl]-2-methyl-L-phenylalanyl]-3-methyl-L-valyl]-L-leucyl]-amino]propylboronic acid;

1(RS)-[[N-[N-[N-[N2-[N-acetyl-1-(2,4-dinitrophenyl)-L-histidyl]-O-benzyl-N6-(p-toluenesulfonyl)-L-arginyl]-2-methyl-L-phenylalanyl]-3-methyl-L-valyl]-L-leucyl]amino]propylboronic acid;

1(RS)-[[N-[N-[N-[N-[N-acetyl-1-(2,4-dinitrophenyl)-L-histidyl]-O-bebenzyl-D-tyrosyl]-2-methyl-L-phenylalanyl]-3-methyl-L-valyl]-L-leucyl]amino]propylboronic acid;

1(RS)-[[N-[N-[N-[N-[N-acetyl-1-(2,4-dinitrophenyl)-L-histidyl]-4-nitro-D-phenylalanyl]-2-methyl-L-phenylalanyl]-3-methyl-L-valyl]-L-leucyl]-amino]propylboronic acid;

1(RS)-[[N-[N-[N-[N-[N-acetyl-1-(2,4-dinitrophenyl)-L-histidyl]-O-bebenzyl-D-seryl]-2-methyl-L- phenylalanyl]-3-methyl-L-valyl]-L-leucyl]amino] propylboronic acid;

1(RS)-[[N-[N-[N-[N-[N-acetyl-1-(2,4-dinitrophenyl)-L-histidyl]-D-2-phenylglycyl]-2-methyl-L-phenylalanyl]-3-methyl-L-valyl]-L-leucyl]-amino] propylboronic acid;

1(RS)-[[N-[N-[N-[N2-[N-acetyl-O-benzyl-L-seryl]-nitro-L-arginyl]-2-methyl-L-phenylalanyl]-3-methyl-L-valyl]-L-leucyl]amino]propylboronic acid;

1(RS)-[[N-[N-[N-[N-[N-acetyl-O-benzyl-L-seryl]-S-benzyl-L-cysteinyl]-2-methyl-L-phenylalanyl]-3-methyl-L-valyl]-L-leucyl]amino]propylboronic acid;

1(RS)-[[N-[N-[N-[N-[N-acetyl-O-benzyl-L-seryl]-D-tryptophyl]-2-methyl-L-phenylalanyl]-3-methyl-L-valyl]-L-leucyl]amino]propylboronic acid;

1(RS)-[[N-[N-[N-[N2-(N-acetyl-S,S-dioxo-L-methionyl]-N6-nitro-L-arginyl]-2-methyl-L-phenylalanyl]-3-methyl-L-valyl]-L-leucyl]amino] propylboronic acid; and 2(RS)-[[N-[N-[N-[N2-(N-acetyl-L-tyrosyl)-N6-nitro-L-arginyl]-2-methyl-L-phenylalanyl]-3-methyl-L-valyl]-L-leucyl]amino]-4,4,4-trifluorobutyraldehyde (SEQ ID NO:5).

Formula ID:

2(RS)-[[N-[N-[N-[N-[N-(3-Carboxypropionyl)-S,S-dioxo-L-methionyl]-D-valyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-S,S-dioxo-S-methyl-L-cysteinyl]-D-valyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-1-(2,4-dinitrophenyl)-L-histidyl]-D-valyl]-2-methyl-L-phenylalanyl]-3-methyl-L-valyl]-L-leucyl]amino]-4,4,4-trifluorobutyraldehyde;

2(RS )-[[N-[N-[N-[N-[N-(3-carboxypropionyl)-L-cysteinyl]-D-valyl]-2-methyl-L-phenylalanyl]-3-methyl-L-valyl]-L-leucyl]amino]-4,4,4-trifluorobutyraldehyde; and 1(RS)-[[N-[N-[N-[N-[N-acetyl-1-(2,4-dinitrophenyl)-L-histidyl]-L-2-cyclohexylglycyl]-2-methyl-L-phenylalanyl]-3-methyl-L-valyl]-L-leucyl]-amino] propylboronic acid.

Formula IE:

2(RS)-[[N-[N-[N-[N-[N-[4-α4-Methylphenyl)butyryl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:6);

2(RS)-[[N-[N-[N-[N-[N-[3-(4-methylbenzoyl) propionyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:7);

2(RS)-[[N-[N-[N-[N-[N-[2-[2-(2-methoxyethoxy) ethoxyacetyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:8);

2(RS)-[[N-[N-[N-[N-[N-[2-(4-oxo-2-thioxo-3-thiazolidinyl)acetyl]-L-α-aspartyl]-L-α-glutamyl]-2-methyl-L-phenylalanyl]-3-methyl-L-valyl]-L-leucyl]-amino]-4,4,4-trifluorobutyraldehyde(SEQ ID NO:9);

2(RS)-[[N-[N-[N-[N-[N-[3-(2-methyl-4-nitro-1-imidazolyl)propionyl]-L-α-aspartyl]-L-α-glutamyl]-2-methyl-L-phenylalanyl]-3-methyl-L-valyl]-L-leucyl]-amino]-4,4,4-trifluorobutyraldehyde (SEQ ID NO:10);

2(RS)-[[N-[N-[N-[N-[N-(5-hexynoyl)-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:11);

2(RS)-[[N-[N-[N-[N-[N-[(6-quinolyl)carbonyl]-L-α-aspartyl]-L-α-glutamyl -2-methyl-L-phenylalanyl]-3-methyl-L-valyl]-L-leucyl]amino]-4,4,4-trifluorobutyraldehyde (SEQ ID NO:12);

2(RS)-[[N-[N-[N-[N-[N-[(6-oxo-3-pyranyl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:13);

2(RS)-[[N-[N-[N-[N-[N-[2-(1,3-benzodioxol-5-yl) acetyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:14);

2(RS)-[[N-[N-[N-[N-[N-[(5,6-dihydro-6,6-dimethyl-4-oxo-4H-pyran-2-yl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:15);

2(RS)-[[N-[N-[N-[N-[N-2-(2-naphthyl)acetyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:16);

2(RS)-[[N-[N-[N-[N-[N-(3-benzamidopropionyl)-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:17);

2(RS)-[[N-[N-[N-[N-[N-[(1,2,3,4-tetrahydro-2,4-dioxo-5-pyrimid-inyl)carbonyl]-L-α-aspartyl]-L-α-glutamyl]-$^2$-methyl-L-phenylalanyl]-3-methyl-L-valyl]-L-leucyl]amino]-4,4,4-trifluorobutyraldehyde (SEQ ID NO:18);

2(RS)-[[N-[N-[N-[N-[N-(3-methyl-2-thenoyl)-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:19);

2(RS)-[[N-[N-[N-[N-N-(2-cyclohexylacetyl)-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:20);

2(RS)-[[N-[N-[N-[N-[N-[2(RS)-(4-nitrophenyl) propionyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:21)

1(RS)-[[N-[N-[N-[N-[N-[(6-oxo-6H-pyran-3-yl) carbonyl]-L-α-aspartyl]-L-α-glutamyl]-2-methyl-L-phenylalanyl]-3-methyl-L-valyl]-L-leucyl]-amino] propylboronic acid (SEQ ID NO:22

1(RS)-[[N-[N-[N-[N-[N-(4-acetamidobutyryl)-L-α-aspartyl]-L-α-glutamyl]-2-methyl-L-phenylalanyl]-3-methyl-L-valyl]-L-leucyl]amino]propylboronic acid (SEQ ID NO:23); and 1(RS)-[[N-[N-[N-[N-[N-(2-acetoxyacetyl)-L-α-aspartyl]-L-α-glutamyl]-2-methyl-L-phenylalanyl]-3-methyl-L-valyl]-L-leucyl]amino]propylboronic acid (SEQ ID NO:24).

Formula IF:

2(RS)-[[N-[N-[N-[N-[N-[2-(2,4,6-Trimethylphenyl) acetyl]-L-seryl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-[(1H-benzotriazol-5-yl) carbonyl-L-seryl]-O-benzyl-D-seryl]-2-methyl-L- phenylalanyl]-3-methyl-L-valyl]-L-leucyl]amino]-4,4,4-trifluorobutyraldehyde;

2(RS)-[[N-[N-[N-[N-[4-(phenylcarbamoyl)-butyryl]-L-seryl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[2-[(4,6-dimethyl-2-pyrimidinyl)thio]acetyl]-L-seryl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[(2-chloro-3-pyridyl)carbonyl]-L-seryl]-O-bebenzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[(9-hydroxy-9-fluorenyl)carbonyl-L-seryl]-O-bebenzyl- D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-[(2-furoyl)-L-seryl]-O-bebenzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[2(RS)-(4-nitrophenyl)propionyl]-L-seryl]-O-bebenzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[2-(2-chlorophenyl)acetyl]-L-seryl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(2-ethoxyacetyl)-L-seryl]-O-benzyl-D-seryl]-2-methyl-L-phenylalanyl]-3-methyl-L-valyl]-L-leucyl]amino]-4,4,4-trifluorobutyraldehyde; and 2(RS)-[[N-[N-[N-[N-[N-[(3-fluoro-4-hydroxyphenyl)acetyl]-L-seryl]-O-bebenzyl-D-seryl -2-methyl-L-phenylalanyl -3-methyl-L-valyl]-L-leucyl]amino]-4,4,4-trifluorobutyraldehyde.

According to the process provided by the present invention, the compounds of formula I hereinbefore and salts of acidic compounds of formula I with bases are manufactured in accordance with one of the following:

a) for the manufacture of a compound of formula I in which E represents CHO, deacetalizing and, where required, deprotecting an acetal of the general formula

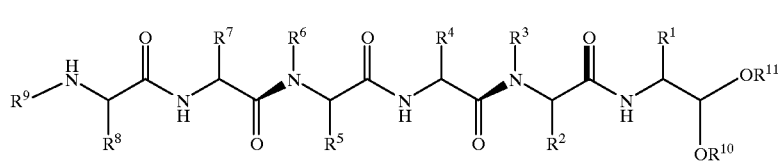

(II)

wherein $R^1$, $R^2$, $R^3$, $R^4$, $R^5$, $R^6$, $R^7$, $R^8$ and $R^9$ have the significance given earlier, provided that any carboxy, hydroxy or aminocarbonyl group(s) present is/are in protected form, and $R^{10}$ and $R^{11}$ each represent lower alkyl;

b) for the manufacture of a compound of formula I in which E represents B(OH)$_2$, ring opening and, where required, deprotecting a substituted dioxaborolane of the general formula

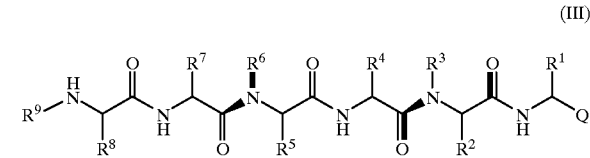

(III)

wherein $R^1$, $R^2$, $R^3$, $R^4$, $R^5$, $R^6$, $R^7$, $R^8$ and $R^9$ have the significance given earlier, provided that any carboxy, hydroxy or aminocarbonyl group(s) present may be in protected form, and Q represents a group of the formula (a)

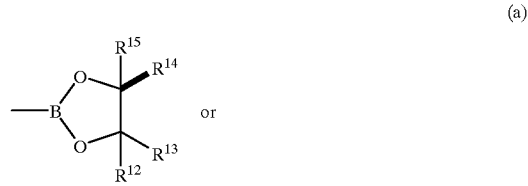

or (b)

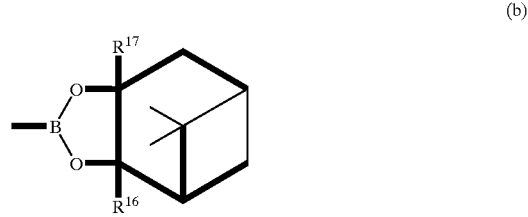

wherein $R^{12}$, $R^{13}$, $R^{14}$, $R^{15}$, $R^{16}$ and $R^{17}$ each represent hydrogen or lower alkyl.

If desired, an acidic compound of formula I may be converted into a salt with a base.

Protected carboxy, hydroxy and aminocarbonyl groups which are present in the acetal starting materials of formula II and which may be present in the substituted dioxaborolane starting materials of formula III are protected with a conventional protecting group known from peptide chemistry. In particular, $R^2$, $R^4$, $R^7$, $R^8$ or $R^9$ can preferably represent tert-butoxycarbonyl-lower alkyl as protected carboxy, $R^2$, $R^4$, $R^5$, $R^7$ $R^8$ or $R^9$ can preferably represent lower alkyl O-tert.butyl ether as protected hydroxy and $R^2$ can preferably represent tritylamino-carbonyl-lower alkyl as protected aminocarbonyl-lower alkyl.

The deacetalization of an acetal of formula II, preferably one in which $R^{10}$ and $R^{11}$ each represent methyl, according to embodiment a) of the inventive process can be carried out in a manner known per se. It is conveniently effected using trifluoroacetic acid or an equivalent strong acid in the presence of an inert organic solvent, such as a halogenated aliphatic hydrocarbon, e.g. dichloromethane, and in the presence of water. Suitably, the deacetalization is carried out at about room temperature. When protected carboxy, hydroxy or aminocarbonyl groups are present in the acetal starting material, these are converted into free carboxy, hydroxy or aminocarbonyl groups under the conditions of the deacetalization.

According to a variant of embodiment a) of the inventive process, an acetal starting material of formula II is bonded to a solid phase peptide synthesis resin. In this case, cleavage from the resin takes place under the conditions used for the deacetalization.

The ring opening of a substituted dioxaborolane of formula III in which Q represents a group of formula (a), preferably one in which $R^{12}$, $R^{13}$, $R^{14}$ and $R^{15}$ each represent methyl, according to embodiment b) of the inventive process can also be carried out using conventional methods. Conveniently, the ring opening is carried out using trifluoroacetic acid or an equivalent strong acid in an inert organic solvent, e.g. a halogenated aliphatic hydrocarbon such as dichloromethane, and optionally in the presence of water. Suitably, the ring opening is carried out at about room temperature. When protected carboxy, hydroxy or aminocarbonyl groups are present in the substituted dioxaborolane starting material, these are converted into free form under the conditions of the ring opening.

The ring opening of a substituted dioxaborolane of formula III in which Q represents a group of formula (b), especially one in which one of $R^{16}$ and $R^{17}$ represents hydrogen and the other represents methyl, according to embodiment b) of the process in accordance with the invention can be carried out in a conventional manner. Conveniently, the ring opening is carried out using a periodate, especially an alkali metal periodate, especially sodium periodate in a buffered aqueous-organic medium, suitably at about room temperature. Advantageously, the medium consists of a mixture of an inert water-miscible organic solvent, e.g. acetone, and aqueous ammonium acetate. Any protected carboxy, hydroxy or aminocarbonyl group(s) present in the substituted dioxaborolane starting material are deprotected in a manner known per se, e.g. by treatment with trifluoroacetic acid, prior to the ring opening.

According to a variant of embodiment b) of the process according to the invention, a substituted dioxaborolane of formula III in which Q represents a group of formula (a) is bonded to a solid phase synthesis resin. The bonding is typically through an alkyl group $R^{12}$, $R^{13}$, $R^{14}$ or $R^{15}$ linked to the resin via an amide bridge. Cleavage from the resin takes place under the conditions used in embodiment b) of the process.

Acidic compounds of formula I can be converted into salts with bases, e.g. alkali metal salts such as sodium or potassium salts, alkaline earth metal salts such as calcium or magnesium salts, salts with organic bases, e.g. salts with amines such as N-ethylpiperidine, procaine or dibenzylamine, or salts with basic amino acids such as salts with arginine or lysine. The formation and isolation of such salts can be carried out according to known methods.

The acetal starting materials of formula II are novel and are to be considered within the scope of the present invention. They can be prepared, for example, by initially reducing a hydroxamate of the general formula

(IV)

wherein $R^1$, $R^{10}$ and $R^{11}$ have the significance given earlier and $Q^1$ represents an amino protecting group, e.g. tert.butoxycarbonyl, with an alkali metal aluminium hydride, e.g. lithium aluminium hydride, treating the product with methanolic hydrochloric acid to give the hydrochloride salt of a compound of the general formula

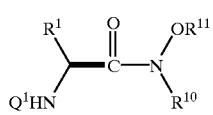

(V)

wherein $R^1$, $R^{10}$ and $R^{11}$ have the significance given earlier, and subsequently either subjecting this to sequential coupling with respective amino acids or subjecting a fragment obtained during such a sequential coupling to further coupling with a peptide derivative of appropriate length. Alternatively, a compound of formula V can be coupled with a suitable pentapeptide.

The aforementioned coupling reactions can be carried out in a manner known per se in peptide chemistry, conveniently using the respective amino acid or di, tri-, tetra- or pentapeptide appropriately protected as described above and also at any amino group present by Fmoc [(9-fluorenyl) methoxycarbonyl] in the presence of hydroxybenzotriazole, 1-(3-dimethylaminopropyl)-3-ethylcarbodiimide hydrochloride and N-methylmorpholine and in an inert organic solvent, e.g. a halogenated hydrocarbon such as dichloromethane.

The hydroxamates of formula IV required for the preparation of the acetal starting materials of formula II are known compounds or analogues of known compounds which can be prepared in an analogous manner to the known compounds.

The acetal starting materials of formula II can also be synthesized from a compound of formula V on a solid phase peptide synthesis resin. This procedure is known and is described in detail in Handbook from Fourth International Symposium on Solid Phase Synthesis and Combinatorial Chemical Libraries, Edinburgh, 1995.

The substituted dioxaborolanes of formula III used as starting materials in embodiment b) of the process according to the invention are novel are to be considered within the scope of the present invention. They can be prepared, for example, as illustrated in Scheme A hereinafter in which $R^1$ and Q have the significance given earlier:

Scheme A

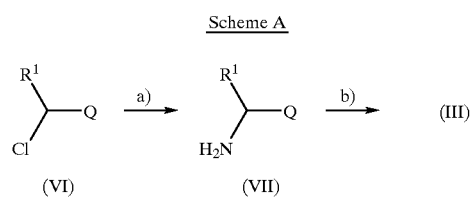

Having regard to Scheme A, in step a) a compound of formula VI is reacted with an alkali metal bis[tri(lower alkyl)silyl]amide, e.g. lithium bis(trimethylsilyl)amide, in an inert organic solvent such as an ether, e.g. diethyl ether or tetrahydrofuran, and then treated with a strong acid, e.g. trifluoroacetic acid, to give a compound of formula VII.

In step b) a compound of formula VII is converted into a compound of formula III either by coupling with a pentapeptide, by sequential coupling with respective amino acids or by coupling a fragment obtained during the sequential coupling with a peptide derivative of the desired length, with the amino acid or peptide used being appropriately protected as described above and also at any amino group present by Fmoc. These coupling reactions can be carried out in a manner known per se in peptide chemistry, for example using the amino acid or peptide in the form of a mixed anhydride formed e.g. with a lower alkyl haloformate such as isobutyl chloroformate and carrying out the coupling in the presence of a suitable base, e.g. a tertiary organic base such as N-methylmorpholine.

Substituted dioxoborolanes of formula III obtained by the foregoing coupling and which carry a protecting group on the substituent at $R^2$, $R^4$, $R^5$, $R^7$, $R^8$ or $R^9$ can be selectively deprotected in a conventional manner, e.g. using trifluoroacetic acid, to the corresponding compounds which carry a free carboxy, hydroxy or aminocarbonyl group on the respective substituent, while retaining the protected boronic acid moiety denoted by Q. These selectively deprotected compounds are also active as inhibitors of proteinases of viral origin and can be used in the treatment of viral infections in the same manner as the compounds of formula I.

Compounds of formula VI can be prepared, for example, from a compound represented by the general formula $$Cl_2CH-Q \qquad (VIII)$$

wherein Q has the significance given earlier, which is a known compound or an analogue of a known compound, by reaction with a compound of the formula $R^1$-MgHal, wherein $R^1$ has the significance given earlier and Hal represents halogen, preferably bromine. The reaction is carried out under the conventional conditions of a Grignard reaction, for example in an inert organic solvent such as an ether, e.g. diethyl ether or tetrahydrofuran. When Q represents a group of formula (b), the reaction is carried out in the presence of zinc chloride.

A compound of formula VI in which $R^1$ represents bromo-lower alkyl or fluoro-lower alkyl and Q represents a group of formula (a) can be prepared, for example, by hydroborating a bromo-or fluoro-lower alkene, e.g. 3-bromopropene or 3-fluoropropene, reacting the hydroboration product with a diol of the formula $R^{12}R^{13}C(OH)-C(OH)R^{14}R^{15}$, wherein $R^{12}$, $R^{13}$, $R^{14}$ and $R^{15}$ have the significance given earlier, e.g. 2,3-dimethyl-2,3-butanediol, and reacting the resulting 2-(bromo-or fluoro-lower alkyl)-1,3,2-dioxaborolane with dichloromethane in the presence of lithium diisopropylamine. The hydroboration can be carried out in a conventional manner, for example using phenylboronic acid at an elevated temperature, e.g. about 100° C., in the absence of a solvent or using borane-dimethyl sulfide complex in the presence of cyclohexene in an inert organic solvent, e.g. dimethoxyethane, at about 0° C. followed by treatment with trimethylamine N-oxide.

A substituted dioxoborolane of formula III in which Q represents a group of formula (a) can also be synthesised on a solid phase peptide synthesis resin. For example, a 4-methylbenzhydryl resin can be reacted with a dioxoborolanyl-valeric acid represented by the general formula

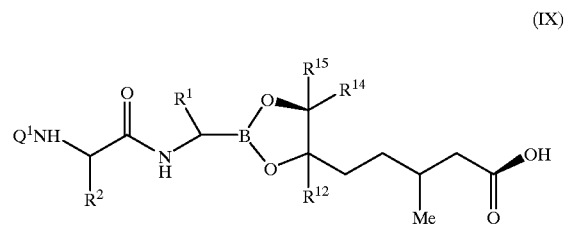

(IX)

wherein $R^1$, $R^2$, $R^{12}$, $R^{14}$, $R^{15}$ and $Q^1$ have the significance given earlier, and the product can be converted into the required resin-bonded starting material by successive deprotection and coupling with a protected amino acid.

Compounds of formula IX can be conveniently prepared by reacting a tert-butyl 6,7-dihydroxy-3,6,7-tri(lower alkyl)-6-octenoate with dichloromethyl diisopropoxyborane, condensing the resulting compound represented by the general formula

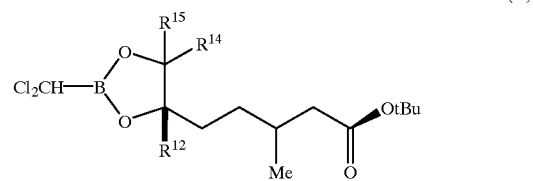

(X)

wherein $R^{12}$, $R^{14}$ and $R^{15}$ have the significance given earlier, with a compound of formula $R^1$MgHal, wherein $R^1$ has the significance given earlier and Hal represents halogen, preferably bromine, under the conditions of a Grignard reaction, reacting the resulting compound represented by the general formula

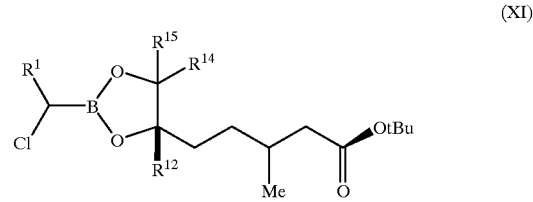

(XI)

wherein $R^1$, $R^{12}$, $R^{14}$ and $R^{15}$ have the significance given earlier, with an alkali metal bis[tri(lower alkyl)silyl]amide, condensing the resulting compound represented by the general formula

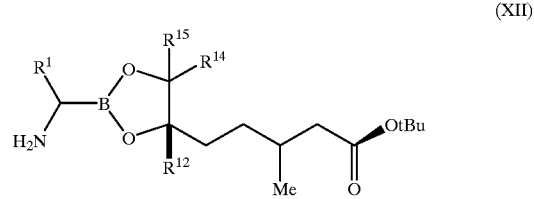

(XII)

wherein $R^1$, $R^{12}$, $R^{14}$ and $R^{15}$ have the significance given earlier, with a protected amino acid represented by the general formula $$Q^2HN-CH(R^2)-COOH \qquad (XIII)$$

wherein R² has the significance given earlier and Q² represents Fmoc, and de-esterifying the resulting compound represented by the general formula

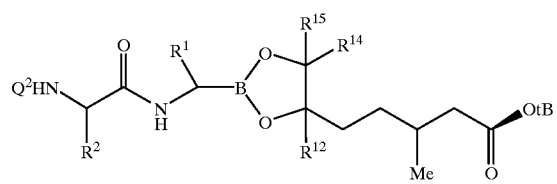

(XIV)

wherein R¹, R², R¹², R¹⁴, R¹⁵ and Q² have the significance given earlier.

As mentioned earlier, the compounds of formula I and salts of acidic compounds of formula I with bases are inhibitors of proteases of viral origin. The activity against one such protease, namely HCV protease, can be demonstrated using the following assay:

Construction of Plasmid for the Expression of MBP-NS3"Gly $_{12}$-NS4A Enzyme in E. coli The nucleotide sequence of this expression plasmid is given in SEQ ID NO:1 appended hereto and the amino acid sequence of its expression product is given in SEQ ID NO:2 appended hereto. It is based on the pMAL®-c2 vector supplied by New England Biolabs, Inc. (32 Tozer Rd., Beverly, Mass., USA). The principle of the construction was to create an in-frame fusion of the maltose binding protein (MBP) gene supplied by the pMAL-c2 vector, and sequences of the HCV genome necessary for NS3 proteinase activity. These HCV sequences were inserted between the EcoRI and HindIII sites of the pMAL-c2 polylinker (positions 2695 and 3556 respectively of the sequence given in SEQ ID NO:1).

HCV sequences were derived from plasmids pDS 3348–4045 and pBFK 3348–6062, described by Bartenschlager et al, 1993 (Journal of Virology, 67, 3835–3844). Regions encompassing the NS3 proteinase domain (amino acids 1007–1219) and the NS4A domain (amino acids 1658–1711) were isolated and inserted into the pMAL-c2 vector using standard recombinant DNA techniques, including the PCR amplification of required sequences. Between the NS3 and NS4A domains, a linker region was constructed using synthetic oligonucleotides (positions 3343–3390; amino acids 606–621). The resulting plasmid was used to transform E. coli (strain MC1061) cells and expression of the MBP-NS3"Gly $_{12}$-NS4A enzyme was induced as described below.

Protein Expression and Purification

E. coli (strain MC1061) cells transformed with the foregoing plasmid were grown in Luria broth containing ampicillin (100 µg/ml) at 37° C. The cells were grown until an optical density of 0.5 at 600 nm had been reached and enzyme expression was then induced by adding 1 mM isopropylthiogalactoside and incubating at 37° C. for a further 3 hours. The cells were harvested by centrifugation and stored at −80° C.

A pellet from 4 of bacterial culture was resuspended in E.coli lysis buffer (20 mM Tris HCl, pH 7.5, containing 150 mM NaCl, 1 mM EDTA and 10 mM dithiothreitol) and cell lysis was achieved by two passages through a French Pressure cell. The clear supernatant obtained by centrifugation (18000 g, 30 minutes) was then applied to an amylose resin column (4×1 cm) (New England Biolabs) which had been equilibrated with ice-cold 50 mM Tris HCl, pH 8.5, containing 200 mM NaCl, 1 mM dithiothreitol and 5% glycerol. The column was washed thoroughly with the equilibration buffer and bound protein was eluted using the equilibration buffer containing 10 mM maltose. Fractions of 1 ml were collected, with fractions containing the enzyme being pooled and stored at −80° C. Enzyme concentration was assayed by the method of M. B. Bradford, Analytical Biochemistry, 1976, vol. 72, p.248.

Assay

Compounds of formula I (routinely prepared as stock solutions in DMSO) were assayed for their ability to inhibit the cleavage of a quenched fluorescence substrate [NS4A/B.F peptide (N-[4-[4-(dimethylamino)phenylazo]benzoyl]-L-α-aspartyl-L-(α-glutamyl-L-methionyl-L-α-glutamyl-L-α-glutamyl-L-cysteinyl-L-alanyl-L-seryl-L-histidyl-N5-[2-(5-sulpho-1-naphthylamino)ethyl]-L-glutamin-amide); Wilkinson et al, Society for General Microbiology Meeting, University of Warwick, England, Mar. 28, 1996] based on the NS4A/4B cleavage site by enzyme MBP-NS3ñGly $_{12}$-NS4A in microtitre plates as follows:

The enzyme (0.4–0.6 µg) was added to a mixture (200 µl final volume) containing 50 mM Tris HCl, pH 8.5, with 1 mM NaCl, 0.1 mM EDTA, 1 mM dithiothreitol, 0.1% Triton X-100, 10 µM NS4A/B.F peptide and the test compound of formula I prepared as a stock solution in DMSO and added to give a 10% final concentration of DMSO. The resulting mixture was incubated at room temperature for 60 minutes and the reaction was terminated by the addition of 100 µl of 2M sodium dihydrogen orthophosphate. The progress of the reaction was evaluated with a Millipore Cytofluor 2350 using an excitation wavelenth of 360 nm and an emission wavelength of 530 nm. The reduction in fluorescence in the presence of the inhibitor was measured, and was plotted against inhibitor concentration. The inhibitor concentration which caused 50% reduction (IC50) was calculated by manual graph analysis.

The results obtained in the foregoing assay with representative compounds of formula I are compiled in the following Table:

TABLE

| Compound of formula I | HCV proteinase IC$_{50}$ (µmol/l) |
|---|---|
| A | 0.2 |
| B | 0.11 |
| C | 0.044 |
| D | 0.14 |
| E | 0.23 |
| F | 0.02 |

Compounds

A= 2(RS)-[[N-[N-[N-[N-(3-Carboxypropionyl)-L-α-aspartyl-L-α-glutamyl]-2-methyl-L-phenylalanyl]-3-methyl-L-valyl]-O-benzyl-L-tyrosyl]amino]-4,4,4-trifluorobutyraldehyde.

B= 2(RS)-[[N-[N-[N-[N-(3-Carboxypropionyl)-L-α-aspartyl]-O-benzyl-L-α-glutamyl]-2-methyl-L-phenylalanyl]-3-methyl-L-valyl]-L-leucyl]amino]-4,4,4-trifluorobutyraldehyde.

C= 2(RS)-[[N-[N-[N-[N2-(N-Acetyl-L-tyrosyl)-N6-nitro-L-arginyl]-2-methyl-L-phenylalanyl]-3-methyl-L-valyl]-L-leucyl]amino]-4,4,4-trifluorobutyraldehyde.

D= 2(RS)-[[N-[N-[N-[N-(3-Carboxypropionyl)-L-cysteinyl]-D-valyl]-2-methyl-L-phenylalanyl]-3-methyl-L-valyl]-L-leucyl]amino]-4,4,4-trifluorobutyraldehyde.

E= 1(RS)-[[N-[N-[N-[N-[N-(4-Acetamidobutyryl)-L-α-aspartyl-L-α-glutamyl]-2-methyl-L-phenylalanyl]-3-methyl-L-valyl]-L-leucyl]-amino]propylboronic acid (SEQ ID NO:23).

F= 2(RS)-[[N-[N-[N-[N-[N-(9-Hydroxy-9-fluorenyl) carbonyl]-L-seryl]-O-benzyl-D-seryl]-2-methyl-L-phenylalanyl]-3-methyl-L-valyl]-L-leucyl]-amino]-4,4,4-trifluorobutyraldehyde.

The compounds of formula I and salts of acidic compounds of formula I with bases can be used as medicaments, e.g. in the form of pharmaceutical preparations. The pharmaceutical preparations can be administered enterally such as orally in the form of tablets, coated tablets, dragées, hard and soft gelatine capsules, solutions, emulsions or suspensions, nasally, e.g. in the form of nasal sprays, or rectally, e.g. in the form of suppositories. They may, however, also be administered parenterally, e.g. in the form of injectable solutions.

The compounds of formula I and their aforementioned salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a salt of an acidic compound of formula I with a base in association with a compatible pharmaceutical carrier are also within the scope of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and salts of acidic compounds of formula I with bases can be used in accordance with the invention as therapeutically active substances, especially as antiviral agents. The dosage can vary within wide limits and will, of course, be fitted to the individual requirements in each particular case. In general, in the case of administration to adults a convenient daily dosage should be about 3 mg to about 3 g, preferably about 10 mg to 1 g. The daily dosage may be administered as a single dose or in divided doses and, in addition, the upper dosage limit referred to earlier may be exceeded when this is found to be indicated.

Finally, the use of compounds of formula I and salts of acidic compounds of formula I with bases for the production of medicaments, especially of antiviral medicaments, is also within the scope of the invention.

The following examples further illustrate the invention, it being understood that it is not intended that the specific details given therein limit the scope thereof.

EXAMPLE 1

0.02 g (0.006 mmol) of 5-[4-[[N-[N-[N-[(9-fluorenyl) methoxycarbonyl]-2-methyl-L-phenylalanyl]-3-methyl-L-valyl]-L-leucy]-N-[3,3,3-trifluoro-1(RS)-(dimethoxymethyl)propyl]amino]methyl]-3,5-dimethoxyphenoxy]-N-(4-methyl-α-(RS)-phenylbenzyl) valeramide-polystyrene conjugate was suspended and agitated in 0.7 ml of dimethylformamide/piperidine (4:1). After 5 minutes the resin was drained and then resuspended in and agitated with 0.7 ml of dimethylformamide/piperidine (4:1) for a further 5 minutes. The resin was then drained and washed five times with 1.5 ml of dimethylformamide.

The resin was then suspended in a solution of 0.028 g (0.06 mmol) of N-[(9-fluorenyl)methoxycarbonyl]-O-benzyl-α-glutamic acid in 0.3 ml of dimethylformamide and then a mixture of 0.019 g (0.06 mmol) of 2-(1H-benzotriazol-1-yl)-1,1,3,3-tetramethyluronium tetrafluoraborate and 0.012 g (0.12 mmol) of N-methylmorpholine dissolved in 0.3 ml of dimethylformamide was added. After agitating for 2 hours the resin was drained and washed five times with 1.5 ml of dimethylformamide.

The resin was resuspended in and agitated with 1.5 ml of dimethylformamide/piperidine (4:1). After 5 minutes the resin was drained and resuspended in and agitated with dimethylformamide/piperidine(4:1) for a further 5 minutes. Then, the resin was drained and washed five times with 1.5 ml of dimethylformamide.

The resin was then suspended in a solution of 0.025 g (0.06 mmol) of N-[(9-fluorenyl)methoxycarbonyl]-O-tert-butyl-L-α-aspartic acid in 0.3 ml of dimethylformamide and then a mixture of 0.019 g (0.06 mmol) of 2-(1H-benzotriazol-1-yl)-1,1,3,3-tetramethyluronium tetrafluoraborate and 0.012 g (0.12 mmol) of N-methylmorpholine dissolved in 0.3 ml of dimethylformamide was added. After agitating for 2 hours the resin was drained and washed five times with 1.5 ml of dimethylformamide.

The resin was resuspended in and agitated with 1.5 ml of dimethylformamide/piperidine (4:1). After 5 minutes, the resin was drained and resuspended in and agitated with dimethylformamide/piperidine (4:1) for a further 5 minutes. Then, the resin was drained and washed five times with 1.5 ml of dimethylformamide.

The resin was then suspended in a solution of 0.01 g (0.06 mmol) of tert-butyl hydrogen succinate in 0.3 ml of dimethylformamide and treated with a mixture of 0.019 g (0.06 mmol) 2-(1H-benzotriazol-1-yl)-1,1,3,3-tetramethyl-uronium tetrafluoroborate and 0.012 g (0.12 mmol) of N-methylmorpholine dissolved in 0.3 ml of dimethylformamide. After agitating for 2 hours the resin was drained and washed 5 times with 1.5 ml of dimethylformamide and then twice with 1.5 ml of dichloromethane.

The resin was treated with 0.8 ml of trifluoroacetic acid/water (19:1) and then agitated for 30 minutes. It was then filtered off and washed with 0.8 ml of trifluoroacetic acid/water (19:1). The combined trifluoroacetic acid/water mixtures were then evaporated in a vacuum centrifuge and the residue was suspended in 0.8 ml of acetonitrile/water (1:1) and freeze dried. There were obtained 6.3 mg of 2(RS)-[[N-[N-[N-[N-[N-(3-carboxypropionyl)-L-α-aspartyl]-O-benzyl-L-α-glutamyl]-2-methyl-L-phenylalanyl]-3-methyl-L-valyl]-L-leucyl]amino]-4,4,4-trifluorobutyraldehyde (1:1 mixture of diastereoisomers) as a white solid; MS: m/e 963.4 [M+H]$^+$.

The starting material was prepared as follows:

i) 18 g (60.0 mmol) of N,O-dimethyl 2(RS)-(tert-butoxyformamido)-4,4,4-trifluorobutyrohydroxamate were dissolved in 230 ml of anhydrous tetrahydrofuran and the solution was cooled to 0° C. 48 ml (48 mmol) of a 1M solution of lithium aluminium hydride in tetrahydrofuran were then added dropwise while maintaining the temperature at 0° C. The mixture was stirred for 10 minutes at 0° C. and then the reaction was quenched by the dropwise addition of saturated potassium hydrogen sulphate solution to pH 1 while maintaining the temperature at below 20° C. The resulting white slurry was stirred vigorously for a further 30 minutes and was then partitioned in three equal aliquots of diethyl ether. The combined diethyl ether fractions were washed with saturated sodium chloride solution, dried over anhydrous magnesium sulphate, filtered and evaporated. The residue was then dissolved in 100 †ml of anhydrous saturated methanolic hydrogen chloride solution and left overnight at 4° C. The mixture was evaporated and the residue was triturated with dichloromethane. The filtrate was evaporated and the residue was chromatographed on silica gel using 5% methanol, 3% acetic acid and 1.5% water in dichloromethane for the elution. There were obtained 8.80 g of 3,3,3-trifluoro-2(RS)-(dimethoxymethyl)-propylamine hydrochloride as a white solid. $^1$H NMR: (CDCl$_3$)δ: 2.60–2.96 (m,2H), 3.49 (d,6H), 3.57–3.69 (q,1H), 4.66 (d,1H), 8.72 (br s,3H).

ii) To a stirred mixture of 5.6 g (25.0 mmol) of 3,3,3-trifluoro-2(RS)-(dimethoxymethyl)-propylamine hydrochloride 3.65 ml of triethylamine, 7.8 g (25.0 mmol) of 4-[4-(ethoxycarbonyl)butoxy]-2,6-dimethoxybenzaldehyde and 25 g of 3 Å molecular sieves in dichloromethane were added 5.8 g (27.5 mmol) of sodium triacetoxyborohydride. After 3 hours the molecular sieves were removed by filtration. The filtrate was then washed with three equal aliquots of saturated sodium bicarbonate solution and dried over anhydrous magnesium sulphate and filtered. The solvent was removed by evaporation and the resulting orange oil was chromatographed on silica gel using 60% ethyl acetate in hexane for the elution. There were obtained 10.4 g of ethyl 5-[4-[[3,3,3-trifluoro-1(RS)-(dimethoxymethyl)propylamino]methyl]-3,5-dimethoxyphenoxy]valerate as a pale orange oil; $^1$H NMR: (CDCl$_3$)δ: 1.25 (t, 3H), 1.78–1.87 (m, 4H), 2.18–2.52 (m, 4H), 2.86–2.92 (m, 1H), 3.33 (d, 6H), 3.77 (s, 6H), 3.81 (d, 2H), 3.96 (t, 2H), 4.13 (q,2H), 4.26 (d, 1H), 6.18 (s, 2H); MS: m/e 482.2 [M+H], 504.2 [M+Na].

iii) A solution of 6.6 g (18.7 mmol) of N-[(9-fluorenyl)-methoxycarbonyl]-L-leucine and 9.7 g (18.7 mmol) of 7-azabenzotriazol-1-yloxy-tris(pyrrolidino)phosphonium hexafluorophosphate in 50 ml of anhydrous dichloromethane was stirred at room temperature for 15 minutes. To this mixture were then added 6.0 g (12.4 mmol) of ethyl 5-[4-[[3,3,3-trifluoro-1(RS)-(dimethoxymethyl)propylamino]methyl]-3,5-dimethoxyphenoxy]valerate and 4.3 ml of (24.8 mmol) diisopropylethylamine. After stirring overnight at 25° C. the mixture was diluted with dichloromethane and washed in sequence with water, 10% citric acid solution, saturated sodium hydrogen carbonate solution and saturated sodium chloride solution, then dried over anhydrous magnesium sulphate and filtered. The solvent was removed by evaporation and the residue was chromatographed on silica gel using 30% ethyl acetate in hexane for the elution. There were obtained 8.06 g of ethyl 5-[4-[[N-[N-[(9-fluorenyl)methoxycarbonyl]-L-leucyl]-N-[3,3,3-trifluoro-1(RS)-(dimethoxymethyl)propyl]amino]methyl]-3,5-dimethoxyphenoxy] valerate; MS: m/e 839.4 [M+Na], 855.3 [M+K].

iv) 8.0 g (9.8 mmol) of 5-[4-[[N-[N-[(9-fluorenyl)methoxycarbonyl]-L-leucyl]-N-[3,3,3-trifluoro-1(RS)-(dimethoxymethyl)propyl]amino]methyl]-3,5-dimethoxyphenoxy]valerate and 40 ml of piperidine were dissolved in 145 ml of dry dichloromethane and the solution was stirred at room temperature for 30 minutes. It was then evaporated in a vacuum and the residue was chromatographed on silica gel using 2% methanol, 49% dichloromethane and 49% hexane followed by 5% methanol, 47.5% dichloromethane and 47.5% hexane for the elution. There were obtained 4.09 †g of ethyl 5-[4-[[N-[3,3,3-trifluoro-1(RS)-dimethoxymethyl)propy]-N-(L-leucyl)amino]methyl]-3,5-dimethoxyphenoxy]valerate as a clear stiff oil; MS: m/e 595 [M+H].

v) A solution of 2.76 g (7.8 mmol) of N-[(9-fluorenyl)-methoxycarbonyl]-3-methyl-L-valine, 1.60 g (8.5 mmol) of 1-(3-dimethylamino npropyl)-3-ethylcarbodiimide hydrochloride and 1.60 g (10.7 mmol) of N-hydroxybenzotriazole in 70 ml of dichloromethane was stirred at 0° C. for 15 minutes. There were then added 4.06 g (7.1 mmol) of ethyl 5-[4-[[N-[3,3,3-trifluoro-1(RS)-(dimethoxymethyl)propyl]-N-(L-leucyl)-amino]methyl]-3,5-dimethoxyphenoxy]valerate and 2.7 ml (21.3 mmol) of N-ethylmorpholine in 70 ml of dichloromethane. After stirring overnight at room temperature the mixture was washed in sequence with 10% citric acid solution, saturated sodium hydrogen carbonate solution and saturated sodium chloride solution, dried over anhydrous magnesium sulphate, filtered and evaporated. The residue was chromatographed on silica gel using 35% ethyl acetate in hexane for the elution. There were obtained 6.11 g of ethyl 5-[4-[[N-[N-[N-[(9-fluorenyl)methoxycarbonyl]-3-methyl-L-valyl]-L-leucyl]-N-[3,3,3-trifluoro-1(RS)-(dimethoxyethyl)propyl]amino]methyl]-3,5-dimethoxy-phenoxy]valerate as a white foam; MS: m/e 952.5 [M+Na], 968.5 [M+K].

vi) 5.8 g (6.3 mmol) of ethyl 5-[4-[[N-[N-[N-[(9-fluorenyl)methoxycarbonyl]-3-methyl-L-valyl]-L-leucyl]-N-[3,3,3-trifluoro-1(RS)-(dimethoxyethyl)-propyl]aminolmethyl]-3,5-dimethoxy-phenoxy] valerate and 18 ml of piperidine were dissolved in 90 ml of dichloromethane and the solution was stirred at room temperature for 1 hour. It was then evaporated and the residue was chromatographed on silica gel using 3% methanol, 48.5% dichloromethane and 48.5% hexane for the elution. There were obtained 4.1 g of ethyl 5-[4-[[N-[3,3,3-trifluro-1 (RS)-(dimethoxymethyl)-propyl]-N-[N-(3-methyl-L-valyl)-L-leucyl]amino]methyl]-3,5-dimethoxyphenoxy]-valerate as a white foam; MS: m/e708.6 [M+H], 730.5 [M+Na].

vii) 4.0 g (5.7 mmol) of ethyl 5-[4-[[N-[3,3,3-trifluoro-1(RS)-(dimethoxy-methyl)propyl]-N-[N-(3-methyl-L-valyl)-L-leucyl]amino]methyl]-3,5-dimethoxyphenoxy]-valerate were dissolved in 40 ml of methanol. 2.4 g (17.3 mmol) of potassium carbonate and 8.0 ml of water were then added and the mixture was stirred for 2 days at room temperature. The solvent was removed by evaporation and the residue was dissolved in 20 ml of water and 20 ml of dioxan. 2.9 g (8.6 mmol) of N-[(9-fluorenyl)-methoxycarbonyloxy]-succinimide were then added and the mixture was stirred for 3 hours. The mixture was adjusted to pH 3 with 10% citric acid and then washed with three equal aliquots of dichloromethane. The combined organic layers were washed with saturated sodium chloride solution, dried over anhydrous magnesium sulphate, filtered and the filtrate was evaporated. The residue was chromatographed on silica gel using 4% tert-butyl methyl ether in dichloromethane for the elution. There were obtained 5.12 g of 5-[4-[[N-[N-[N-[(9-fluorenyl) methoxycarbonyl]-3-methyl-L-valyl]-L-leucyl]-N-[3,3,3-trifluoro-1(RS)-(dimethoxymethyl)propyl]amino] methyl]-3,5-dimethoxyphenoxylvaleric acid as a white foam; MS: m/e 870.8 [M+H—MeOH], 888.7 [M+H—$CH_3$], 889.7 [M—$CH_3$]902.7 [M+H], 924.7 [M+Na].

viii) 5.4 g (5.4 mmol) of 4-methylbenzhydrylamine resin were swollen in 30 ml of dimethylformamide, excess solvent was drained from the resin and it was then washed twice with 20 ml dimethylformamide/N-methylmorpholine (9:1). The resin was then resuspended in 10 ml of dimethylformamide containing 4.98 g (5.4 mmol) of 5-[4-[[N-[N-[N-[(9-fluorenyl) methoxycarbonyl]-3-methyl-L-valyl]-L-leucyl]-N-[3,3,3-trifluoro-1(RS)-(dimethoxymethyl)propyl]amino] methyl-3,5-dimethoxyphenoxy]valeric acid and 1.74 g (5.4 mmol) of 2-(1H-benzotriazol-1-yl)-1,1,3,3-tetramethyluronium tetrafluoraborate. Thereto were added 1.18 ml (10.8 mmol) of N-methylmorpholine dissolved in 10 ml of dimethylformamide. The resulting mixture was agitated for 2 hours and the resin was then drained and washed five times with 30 ml of dimethylformamide. The resin was then resuspended in 30 ml of dimethylformamide containing 2.03 ml (21.6 mmol) of acetic anhydride and 2.96 ml (27 mmol) of N-methylmorpholine. This mixture was agitated for 30 minutes and the resin was then drained and washed five times with 30 ml of dimethylformamide each time. The resin was resuspended in and agitated in 30 ml of dimethylformamide/piperidine (4:1). After 5 minutes the resin was drained, resuspended and again agitated in the foregoing dimethylform-amide/piperidine mixture for a further 5 minutes. The resin was then drained and washed five times with 30 ml of dimethylformamide.

ix) A solution of 3.2 g (8.1 mmol) of N-[(9-fluorenyl) methoxycarbonyl]-3-(2-methylphenyl)-L-alanine and 2.17 g (6.75 mmol) of 2-(1H-benzotriazol-1-yl)-1,1,3,3-tetramethyluronium tetrafluoroborate in 22 ml of dimethylformamide was added to the resin from paragraph viii) and subsequently 1.5 ml (13.5 mmol) of N-methylmorpholine were added. The mixture was agitated for 30 minutes and then the resin was drained and washed five times with 30 ml of dimethylformamide, twice with 30 ml of dichloromethane, twice with 30 ml of ethyl acetate and twice with 30 ml of diethyl ether. After drying there were obtained 8.95 g of 5-[4-[[N-[N-[N-[(9-fluorenyl) methoxycarbonyl]-2-methyl-L-phenylalanyl]-3-methyl-L-valyl]-L-leucyl]-N-[3,3 ,3-trifluoro-1(RS)-(dimethoxy-methyl)propyl]amino]methyl]-3,5-dimethoxyphenoxy]-N-(4-methyl-α-(RS)-phenylbenzyl)valeramide-polystyrene conjugate as a pale brown solid (0.31 mmol/g loading estimated by quantitation of dibenzofulvene at 301 nm).

EXAMPLE 2

In an analogous manner to Example 1, by replacing N-[(9-fluorenyl)methoxycarbonyl]-O-benzyl-α-glutamic acid with N-[( 9-fluorenyl)methoxycarbonyl]-N6-nitro-L-arginine there was obtained 2(RS)-[[N-[N-[N-[N-[N-(3-carboxypropionyl)-L-α-aspartyl]-N6-nitro-L-arginyl]-2-methyl-L-phenylalanyl]-3-methyl-L-valyl]-L-leucyl] amino]-4,4,4-trifluorobutyraldehyde as a white solid; MS: m/e 945.5 [M+H].

EXAMPLE 3

In an analogous manner to Example 1, by replacing N-[(9-fluorenyl)methoxycarbonyl]-O-benzyl-α-glutamic acid with N-[(9-fluorenyl)-methoxycarbonyl]-S-(acetamidomethyl)-L-cysteine there was obtained 2(RS)-[[N-[N-[N-[N-[N-(3-carboxypropionyl)-L-α-aspartyl]-S-(acetamidomethyl)-L-cysteinyl]-2-methyl-L-phenylalanyl]-3-methyl-L-valyl]-L-leucyl]amino]-4,4,4-trifluorobutyraldehyde as a white solid; MS m/e 918.4 [M+H].

EXAMPLE 4

In an analogous manner to Example 1, by replacing N-[(9-fluorenyl)methoxycarbonyl]-O-benzyl-α-glutamic acid with N-[(9-fluorenyl)methoxycarbonyl]-S-benzyl-L-cysteine there was obtained 2(RS)-[[N-[N-[N-[N-[N-(3-carboxypropionyl)-L-α-aspartyl]-S-benzyl-L-cysteinyl]-2-methyl-L-phenylalanyl]-3-methyl-3-L-valyl]-L-leucyl]amino]-4,4,4-trifluorobutyraldehyde as a white solid; MS: m/e 937.4 [M+H].

EXAMPLE 5

In an analogous manner to Example 1, by replacing N-[(9-fluorenyl)methoxycarbonyl]-O-benzyl-α-glutamic acid with N-[(9-fluorenyl)methoxycarabonyl]-D-valine and replacing N-[(9-fluorenyl)methoxycarbonyl]-o-t-butyl-L-α-aspartic acid with N-[(9-fluorenyl)methoxycarbonyl]-S,S-dioxo-L-methionine there was obtained 2(RS)-[[N-[N-[N-[N-[N-(3-carboxypropionyl)-S,S-dioxo-L-methionyl]-D-valyl]- 2-methyl-L-phenylalanyl]-3-methyl-L-valyl]-L-leucyl]amino]-4,4,4-trifluorobutyraldehyde as a white solid; MS: m/e 891.5 [M+H].

EXAMPLE 6

In an analogous manner to Example 1, by replacing N-[(9-fluorenyl)methoxycarbonyl]-O-benzyl-α-glutamic acid with N-[(9-fluorenyl)methoxycarbonyl]-D-valine and replacing N-[(9-fluorenyl)methoxycarbonyl]-o-t-butyl-L-α-aspartic acid with N-[(9-fluorenyl)methoxycarbonyl]-S,S-dioxo-S-methyl-L-cysteine there was obtained 2(RS)-[[N-[N-[N-[N-(3-carboxypropionyl)-S,S-dioxo-S-methyl-L-cysteinyl]-D-valyl]-2-methyl-L-phenylalanyl]-3-methyl-L-valyl]-L-leucyl]amino]-4,4,4-trifluorobutyraldehyde as a white solid; MS: m/e 877.5 [M+H].

EXAMPLE 7

In an analogous manner to Example 1, by replacing N-[(9-fluorenyl)methoxycarbonyl]-O-benzyl-α-glutamic acid with N-[(9-fluorenyl)methoxycarbonyl]-D-valine and by replacing N-[(9-fluorenyl)methoxycarbonyl]-O-bet-butyl-L-α-aspartic acid with N-[(9-fluorenyl) methoxycarbonyl]-1-(2,4-dinitrophenyl)-L-histidine there was obtained 2(RS)-[[N-[N-[N-[N-[N-(3-carboxypropionyl)-1-(2,4-dinitrophenyl)-L-histidyl]-D-valyl]-2-methyl-L-phenyl-alanyl]-L-leucyl]amino]-4,4,4-trifluorobutyraldehyde as a white solid; MS: m/e 1031.5 [M+H].

EXAMPLE 8

In an analogous manner to Example 1, by replacing N-[(9-fluorenyl)methoxycarbonyl]-O-bebenzyl-α-glutamic acid with N-[(9-fluorenyl)methoxycarbonyl]-O-bet-butyl-L-α-aspartic acid with N-[(9-fluorenyl)methoxycarbonyl]-S-t-butyl-L-cysteine there was obtained 2(RS)-[[N-[N-[N-[N-[N-(3-carboxypropionyl)-L-cysteinyl]-D-valyl]- 2-methyl-L-phenylalanyl]-3-methyl-L-valyl]-L-leucyl]amino]-4,4,4-trifluorobutyraldehyde as a white solid; MS: m/e 887.5 [M+H].

EXAMPLE 9

In an analogous manner to Example 1, by replacing N-[(9-fluorenyl)methoxycarbonyl]-O-benzyl-α-glutamic acid with N-[(9-fluorenyl)methoxycarbonyl]-3-(3-thenyl)-D-alanine there was obtained 2(RS)-[[N-[N-[N-[N-(3-carboxypropionyl)-L-α-aspartyll -3-(3-thenyl)-D-alanyl]-2-methyl-L-10 phenylalanyl]-3-methyl-L-valyl]-L-leucyl] amino]-4,4,4-trifluoro-butyraldehyde as a white solid; MS: m/e 897.2 [M+H].

EXAMPLE 10

In an analogous manner to Example 1, by replacing N-[(9-fluor-15 enyl)methoxycarbonyl]-O-benzyl-α-glutamic acid with N-[(9-fluorenyl)methoxycarbonyl]-D-N-(tert-butoxycarbonyl)-tryptophan there was obtained 2(RS)-[[N-[N-[N-[N-[N-(3-carboxypropionyl)-L-α-aspartyl]-D-tryptophyl]-2-methyl-L-phenylalanyl]-3-methyl-L-valyl-L-leucyl]amino]-4,4 ,4-trifluorobutyraldehyde as a white solid; MS: m/e 930.4 [M+H].

EXAMPLE 11

In an analogous manner to Example 1, by replacing N-[(9-fluorenyl)methoxycarbonyl]-O-benzyl-α-glutamic acid with N-[(9-fluorenyl)methoxycarbonyl]-O-benzyl-D-tyrosine there was obtained 2(RS)-[[N-[N-[N-[N-[N-25 (3-carboxypropionyl)-L-α-aspartyl]-O-benzyl-D-tyrosyl]-2-methyl-L-phenylalanyl]-3-methyl-L-valyl]-L-leucyl] amino]-4,4,4-trifluorobutyraldehyde as a white solid; MS: m/e 997.4 [M+H].

EXAMPLE 12

In an analogous manner to Example 1, by replacing N-[(9-fluor-enyl)methoxycarbonyl]-O-benzyl-α-glutamic acid with N-[(9-fluorenyl)-ethoxycarbonyl]-S-(4-methoxybenzyl)-D-cysteine there was obtained 2(RS)-[[N-[N-[N-[N-[N-(3-carboxypropionyl)-L-α-aspartyl]-S-(4-methoxybenzyl )-D-cysteinyl]-2-methyl-L-phenylalanyl]-3-methyl-L-valyl]-L-leucyl]amino -4,4,4-trilfluorobutyraldehyde as a solid; MS: m/e 967.3 [M+H].

EXAMPLE 13

In an analogous manner to Example 1, by replacing N-[(9-fluorenyl)methoxycarbonyl]-O-benzyl-α-glutamic acid with [(9-fluorenyl)methoxycarbonyl]-O-benzyl-D-serine there was obtained 2(RS)-[[N-[N-[N-[N-[N-(3-carboxypropionyl)-L-α-aspartyl]-O-benzyl-D-seryl]-2-methyl-L-phenylalanyl -3-methyl-L-valyl]-L-leucyl]amino]-4,4,4-trifluorobutyraldehyde as a white solid; MS: m/e 921.3 [M+H].

EXAMPLE 14

In an analogous manner to Example 1, by replacing N-[(9-fluorenyl)methoxycarbonyl]-O-benzyl-α-glutamic acid with N-[(9-fluorenyl)methoxycarbonyl]-O-benzyl-D-threonine there was obtained 2(RS)-[[N-[N-[N-[N-[N-(3-carboxypropionyl)-α-aspartyl]-O-benzyl-D-threonyl]-2-methyl-L-phenylalanyl]-3-methyl-L-valyl]-L-leucyl]amino]-4,4,4-trifluorobutyraldehyde as a white solid; MS: m/e 935.4 [M+H].

EXAMPLE 15

In an analogous manner to Example 1, by replacing N-[(9-fluorenyl)methoxycarbonyl]-O-benzyl-α-glutamic acid with N-[(9-fluorenyl)methoxycarbonyl]-O-bebenzyl-serine, by replacing N-[(9-fluorenyl)methoxycarbonyl]-O-bet-butyl-L-α-aspartic acid with N-[( 9-fluorenyl)methoxycarbonyl]-O-bet-butyl-L-serine and by replacing tert-butyl hydrogen succinate with 2-(2,4,6-trimethylphenyl)acetic acid there was obtained 2(RS)-[[N-[N-[N-[N-[N-[2-(2,4,6-trimethylphenyl)acetyl]-L-seryl]-O-bebenzyl-D-seryl]-2-methyl-L-phenylalanyl]-3-methyl-L-valyl]-L-leucyl] amino]-4,4,4-trifluorobutyraldehyde as a white solid; MS: m/e 953.4 [M+H].

EXAMPLE 16

In an analogous manner to Example 1, by replacing N-[(9-fluorenyl)methoxycarbonyl]-O-bebenzyl-α-glutamic acid with N-[(9-fluorenyl)methoxycarbonyl]-O-bebenzyl-D-serine, by replacing N-[9-fluorenyl)methoxycarbonyl]-O-bet-butyl-L-α-aspartic acid with N-[(9-fluorenyl) methoxycarbonyl]-O-bet-butyl-L-serine and by replacing tert-butyl hydrogen succinate with 4-chloro-3-sulphamoylbenzoic acid was obtained 2(RS)-[[N-[N-[N-[N-[N-(4-chloro-3-sulphamoylbenzoyl)-L-seryl]-O-bebenzyl-D-seryl]-2-methyl-L-phenylalanyl]-3-methyl-L-valyl]-L-leucyl]amino]-4,4,4-trifluorobutyraldehyde as a white solid; MS: m/e 1010.3 [M+H].

EXAMPLE 17

In an analogous manner to Example 1, by replacing N-[(9-fluorenyl)methoxycarbonyl]-O-bebenzyl-α-glutamic acid with N-[(9-fluorenyl)methoxycarbonyl]-O-bebenzyl-D-serine, by replacing N-[(9-fluorenyl)methoxycarbonyl]-O-bet-butyl-L-α-aspartic acid with N-[(9-fluorenyl) methoxycarbonyl]-O-butyl-L-serine and by replacing tert-butyl hydrogen succinate with benzotriazole-5-carboxylic acid there was obtained 2(RS)-[[N-[N-[N-[N-[N-[(1H-benzotriazol-5-yl)carbonyl-L-seryl]-O-bebenzyl-D-seryl]-2-methyl-L-phenylalanyl]-3-methyl-L-valyl]-L-leucyl] amino]-4,4,4-trifluorobutyraldehyde as a white solid; MS m/e 938.4 [M+H].

EXAMPLE 18

In an analogous manner to Example 1, by replacing N-[(9-fluorenyl)methoxycarbonyl]-O-bebenzyl-α-glutamic acid with N-[(9-fluorenyl)methoxycarbonyl]-O-bebenzyl-D-serine, by replacing N-[(9-fluorenyl)-5 methoxycarbonyl]-O-bet-butyl-L-α-aspartic acid with N-[(9-fluorenyl)methoxycarbonyl]-O-bet-butyl-L-serine and by replacing tert-butyl hydrogen succinate with 4-(phenylcarbamoyl)butyric acid there was obtained 2(RS)-[[N-[N-[N-[N-[N-[4-(phenylcarbamoyl)-butyryl]-L-seryl]-O-bebenzyl-D-seryl]-2-methyl-L-phenylalanyl]-3-methyl-L-valyl]-L-leucyl]amino]-4,4,4-trifluorobutyraldehyde as a white solid; MS: m/e 982.4 [M+H].

EXAMPLE 19

In an analogous manner to Example 1, by replacing N-[(9-fluorenyl)methoxycarbonyl]-O-bebenzyl-α-glutamic acid with N-[(9-flurenyl)-15 methoxycarbonyl]-O-bebenzyl-D-serine, by replacing N-[(9-fluorenyl)

methoxycarbonyl]-O-bet-butyl-L-α-aspartic acid with [(9-fluorenyl)methoxycarbonyl]-O-bet-butyl-L-serine and by replacing tert-butyl hydrogen succinate with 2-[(4,6-dimethyl-2-pyrimidinyl)thio]acetic acid there was obtained 2(RS)-[[N-[N-[N-[N-[N-[2-[(4,6-dimethyl-2-pyrimidinyl) thio]acetyl]-L-seryl]-O-20 benzyl-D-seryl]-2-methyl-L-phenylalanyl]-3-methyl-L-valyl]-L-leucyl]amino]-4,4,4-trifluorobutyraldehyde as a white solid; m/e 973.4 [M+H].

EXAMPLE 20

In an analogous manner to Example 1, by replacing N-[(9-fluor-25 enyl)methoxycarbonyl]-O-bebenzyl-α-glutamic acid with N-[(9-fluorenyl)methoxycarbonyl]-O-bebenzyl-D-serine, by replacing N-[(9-fluorenyl) methoxycarbonyl]-O-bet-butyl-L-α-aspartic acid with N-[(9-fluorenyl)methoxycarbonyl]-O-bet-butyl-L-serine and by replacing tert-butyl hydrogen succinate with 2-chloronicotinic acid there was obtained 2(RS)-[[N-[N-[N-[N-[N-[(2-chloro-3-pyridyl)carbonyl]-L-seryl]-O-bebenzyl-D-seryl]-2-methyl-L-phenylalanyl]-3-methyl-L-valyl]-leucyl]amino]-4,4,4-trifluorobutyraldehyde as a white solid; MS: m/e 932.3 [M+H].

EXAMPLE 21

In an analogous manner to Example 1, by replacing N-[(9-fluorenyl)methoxycarbonyl]-O-bebenzyl-α-glutamic acid with N-[(9-fluorenyl)methoxycarbonyl]-O-bebenzyl-D-serine, by replacing N-[(9-fluorenyl)methoxycarbonyl]-O-bet-butyl-L-α-aspartic acid with N-[(9-fluorenyl) methoxycarbonyl]-O-bet-butyl-L-serine and by replacing tert-butyl hydrogen succinate by 4-acetamidobenzoic acid there was obtained 2(RS)-[[N-[N-[N-[N-[N-(4-acetamidobenzoyl)-L-seryl]-O-bebenzyl-D-seryl]-2-methyl-L-phenylalanyl]-3-methyl-L-leucyl]amino]-4,4,4-trifluorobutyraldehyde as a white solid; MS: m/e 954.4 [M+H].

EXAMPLE 22

In an analogous manner to Example 1, by replacing N-[(9-fluorenyl)methoxycarbonyl]-O-bebenzyl-α-glutamic acid with N-[(9-fluorenyl)methoxycarbonyl]-O-bebenzyl-D-serine, by replacing N-[(9-fluorenyl)methoxycarbonyl]-O-bet-butyl-L-α-aspartic acid with N-[(9-fluorenyl) methoxycarbonyl]-O-bet-butyl-L-serine and by replacing tert-butyl hydrogen succinate with 9-hydroxy-9-fluorenylcarboxylic acid there was obtained 2(RS)-[[N-[N-[N-[N-[(9-hydroxy-9-fluorenyl)carbonyl]-L-seryl -O-bebenzyl-D-seryl]-2-methyl-L-phenylalanyl]-3-methyl-L-valyl]-L-leucyl]amino]-4,4,4-trifluorobutyraldehyde as a white solid; MS: m/e 1001.3 [M+H].

EXAMPLE 23

In an analogous manner to Example 1, by replacing N-[(9-fluorenyl)methoxycarbonyl]-O-bebenzyl-α-glutamic acid with N-[( 9-fluorenyl)methoxycarbonyl]-O-bebenzyl-D-serine, by replacing N-[(9-fluorenyl)methoxycarbonyl]-O-bet-butyl-L-α-aspartic acid with N-[(9-fluorenyl) methoxycarbonyl]-O-bet-butyl-L-serine and by replacing tert-butyl hydrogen succinate with dihydro-L-orotic acid there was obtained 2(RS)-[[N-[N-[N-[N-[N-[(hexahydro-2, 6-dioxo-4(S)-pyrimidinyl)carbonyl]-L-seryl]-O-bebenzyl-D-seryl]-2-methyl-L-phenylalanyl]-3-methyl-L-valyl]-L-leucyl]amino]-4,4,4-trifluorobutyraldehyde as a white solid; MS: m/e 933.4 [M+H].

EXAMPLE 24

In an analogous manner to Example 1, by replacing N-[(9-fluorenyl)methoxycarbonyl]-O-bebenzyl-α-glutamic acid with N-[(9-fluorenyl)methoxycarbonyl]-O-bebenzyl-D-serine, by replacing N-[(9-fluorenyl)methoxycarbonyl]-O-bet-butyl-L-α-aspartic acid with [(9-fluorenyl) methoxycarbonyl]-O-bet-butyl-L-serine and by replacing tert-butyl hydrogen succinate with 2-furoic acid there was obtained 2(RS)-[[N-[N-[N-[N-[N-(2-furoyl)-L-seryl]-O-bebenzyl-D-seryl]-2-methyl-L-phenylalanyl]-3-methyl-L-valyl]-L-leucyl]amino]-4,4,4-trifluorobutyraldehyde as a white solid; MS: m/e 887.3 [M+H].

EXAMPLE 25

In an analogous manner to Example 1, by replacing N-[(9-fluorenyl)methoxycarbonyl]-O-bebenzyl-α-glutamic acid with N-[(fluorenyl)methoxycarbonyl]-O-bebenzyl-D-serine, by replacing N-[(9-fluorenyl)methoxycarbonyl]-O-bet-butyl-L-α-aspartic acid with N-[(9-fluorenyl) methoxycarbonyl]-O-bet-butyl-L-serine and by replacing tert-butyl hydrogen succinate with 2(RS)-(4-nitrophenyl) propionic acid there was obtained 2(RS)-[[N-[N-[N-[N-[N-[2(RS)-(4-nitrophenyl)propionyl]-L-seryl]-O-bebenzyl-D-seryl -2-methyl-L-phenylalanyl]-3-methyl-L-valyl]-L-leucyl]amino]-4,4,4-trifluorobutyraldehyde as a white solid; MS: m/e 970.4 [M+H].

EXAMPLE 26

In an analogous manner to Example 1, by replacing N-[(9-fluorenyl)methoxycarbonyl]-L-leucine with N-[(9-fluorenyl)methoxycarbonyl]-O-benzyl-L-tyrosine and by replacing N-[(9-fluorenyl)methoxycarbonyl]-O-benzyl-α-glutamic acid with N-[(9-fluorenyl)methoxycarbonyl]-O-bet-butyl-L-α-glutamic acid there was obtained 2(RS)-[[N-[N-[N-[N-(3-carboxypropionyl)-L-α-aspartyl]-L-α-glutamyl]-2-methyl-L-phenylalanyl -3-methyl-L-valyl -O-bebenzyl-L-tyrosyl]amino]-4,4,4-trifluorobutyraldehyde as a white solid; MS: m/e 1013.3 [M+H].

EXAMPLE 27

In an analogous manner to Example 1, by replacing N-[(9-fluorenyl)methoxycarbonyl]-L-leucine with N-[(9-fluorenyl)methoxycarbonyl]-O-(2,6-dichlorobenzyl)-L-tyrosine and by replacing N-[(9-fluorenyl) methoxycarbonyl]-O-benzyl-α-glutamic acid with N-[(9-fluorenyl)methoxycarbonyl]-O-t-butyl-L-alpha-glutamic acid there was obtained 2(RS)-[[N-[N-[N-[N-[N-(3-carboxypropionyl)-L-α-aspartyll -L-α-glutamyl]-2-methyl-L-phenylalanyl]-3-methyl-L-valyl]-O-(2,6-dichlorobenzyl)-L-tyrosyl]amino]-4,4,4-trifluorobutyraldehyde as a white solid; 20 MS: m/e 1081.2 [M+H].

EXAMPLE 28

In an analogous manner to Example 1, by replacing N-[(9-fluorenyl)methoxycarbonyl]-L-leucine with N-[(9-fluorenyl)methoxycarbonyl]-2-(3-thienyl)-L-alanine and by replacing N-[(9-fluorenyl)methoxycarbonyl]-O-bebenzyl-α-glutamic acid with N-[(9-fluorenyl)methoxycarbonyl]-O-bet-butyl-L-α-glutamic acid there was obtained 2(RS)-[[N-[N-[N-[N-(3-carboxypropionyl)-L-α-aspartyl]-L-α-glutamyl]-2-methyl-L-phenylalanyl]-3-methyl-L-valyl -2-(3-thienyl)-L-alanyl]amino]- 4,4,4-trifluorobutyraldehyde as a white solid; MS: m/e 913.4 [M+H].

EXAMPLE 29

In an analogous manner to Example 1, by replacing N-[(9-fluorenyl)methoxycarbonyl]-O-benzyl-α-glutamic acid with N-[(9-fluorenyl)methoxycarbonyl]-O-benzyl-D-

EXAMPLE 30

In an analogous manner to Example 1, by replacing N-[(9-fluorenyl)methoxycarbonyl]-O-benzyl-α-glutamic acid with N-[(9-fluorenyl)methoxycarbonyl]-N6-nitro-L-arginine, by replacing N-[(9-fluorenyl)methoxycarbonyl]-O-t-butyl-L-α-aspartic acid with N-[(9-fluorenyl) methoxycarbonyl]-O-t-butyl-L-serine and by replacing tert-butyl hydrogen succinate together with 2-(1H-benzotriazol-1-yl)-1,1,3,3-tetramethyluronium tetrafluoroborate with acetic anhydride there was obtained 2(RS)-[[N-[N-[N-[N2-(N-acetyl-L-tyrosyl)-N6-nitro-L-arginyl]-2-methyl-L-phenylalanyl]-3-methyl-L-valyl]-L-leucyl]amino]-4,4,4-trifluorobutyraldehyde (SEQ ID NO:5 as a white solid: MS: m/e 935.5 [M+H].

EXAMPLE 31

In an analogous manner to Example 1, by replacing N-[(9-fluorenyl)methoxycarbonyl]-O-benzyl-α-glutamic acid with N-[(9-fluorenyl)methoxycarbonyl]-O-bebenzyl-D-serine, by replacing N-[( 9-fluorenyl)methoxycarbonyl]-O-bet-butyl-L-α-aspartic acid with N-[(9-fluorenyl) methoxycarbonyl]-O-bet-butyl-L-serine and by replacing tert-butyl hydrogen succinate with 2-(2-chlorophenyl)acetic acid there was obtained 2(RS)-[[N-[N-[N-[N-[N-[2-(2-chlorophenyl)acetyl]-L-seryl]-O-bebenzyl-D-seryl]-2-methyl-L-phenylalanyl]-3-methyl-L-valyl]-L-leucyl]amino]-4,4,4-trifluorobutyraldehyde as a white solid; MS: m/e 945.4 [M+H].

EXAMPLE 32

In an analogous manner to Example 1, by replacing N-[(9-fluorenyl)methoxycarbonyl]-O-benzyl-α-glutamic acid with N-[(9-fluorenyl)methoxycarbonyl]-O-benzyl-D-serine, by replacing N-[(9-fluorenyl)methoxycarbonyl]-O-t-butyl-L-α-aspartic acid with N-[(9-fluorenyl) methoxycarbonyl]-O-t-butyl-L-serine and by replacing tert-butyl hydrogen succinate with 2-ethoxyacetic acid there was obtained 2(RS)-[[N-[N-[N-[N-[N-(2-ethoxyacetyl)-L-seryl]-O-bebenzyl-D-seryl]-2-methyl-L-phenylalanyl]-3-methyl-L-valyl]-L-leucyl]amino]-4,4,4-trifluorobutyraldehyde as a white solid; MS: m/e 879.4 [M+H].

EXAMPLE 33

In an analogous manner to Example 1, by replacing N-[(9-fluorenyl)methoxycarbonyl]-O-bebenzyl-α-glutamic acid with N-[(9-fluorenyl)methoxycarbonyl]-O-bebenzyl-D-serine, by replacing N-[(9-fluorenyl)methoxycarbonyl]-O-bet-butyl-L-α-aspartic acid with N[(9-fluorenyl) methoxycarbonyl]-O-bet-butyl-L-serine and tert-butyl hydrogen succinate with 3-hydroxy-4,5-dimethoxybenzoic acid there was obtained 2(RS)-[[N-[N-N-[LN [N-(3-hydroxy-4,5-dimethoxybenzoyl)-L-seryl]-O-benzyl-D-seryl]-2-methyl-L-phenylalanyl]-3-methyl-L-valyl]-L-leucyl]amino]-4,4,4-trifluorobutyraldehyde as a white solid; MS: m/e 973.4 [M+H].

serine, by replacing N-[(9-fluorenyl)methoxycarbonyl]-O-t-butyl-L-α-aspartic acid with N-[(9-fluorenyl) methoxycarbonyl]-O-t-butyl-L-serine and by replacing tert-butyl hydrogen succinate with 4-(2-thenoyl)butyric acid there was obtained 2(RS)-[[N-[N-[N-[N-[N-[4-(2-thenoyl)butyryl]-L-seryl]-O-benzyl-D-seryl]-2-methyl-L-phenylalanyl]-3-methyl-L-valyl]-L-leucyl]amino]-4,4,4-trifluorobutyraldehyde as a white solid; m/e 973.4 [M+H].

EXAMPLE 34

In an analogous manner to Example 1, by replacing N-[(9-fluorenyl)methoxycarbonyl]-O-benzyl-α-glutamic acid with N-[(9-fluorenyl)methoxycarbonyl]-O-benzyl-D-serine, by replacing N-[(9-fluorenyl)methoxycarbonyl]-O-t-butyl-L-α-aspartic acid with N-[(9-fluorenyl) methoxycarbonyl]-O-t-L-serine and by replacing tert-butyl hydrogen succinate with 2-ethylbutyric acid there was obtained 2(RS)-[[N-[N-[N-[N-[N-(2-ethylbutyryl)-L-seryl]-O-benzyl-D-seryl]-2-methyl-L-phenylalanyl]-3-methyl-L-methyl-L-valyl]-L-leucyl]amino]-4,4,4-trifluorobutyraldehyde as a white solid; MS: m/e 891.4 [M+H].

EXAMPLE 35

In an analogous manner to Example 1, by replacing N-[(9-fluorenyl)methoxycarbonyl]-O-benzyl-α-glutamic acid with N-[(9-fluorenyl)methoxycarbonyl]-O-benzyl-D-serine, by replacing N-[(9-fluorenyl)methoxycarbonyl]-O-t-butyl-L-α-aspartic acid with N-[(9-fluorenyl) methoxycarbonyl]-O-t-butyl-L-serine and by replacing tert-butyl hydrogen succinate with 2-(3-fluoro-4-hydroxyphenyl)acetic acid there was obtained 2(RS)-[[N-[N-[N-N-[N-[(3-fluoro-4-hydroxyphenyl)acetyl]-L-seryl]-O-benzyl-D-seryl]-2-methyl-L-phenylalanyl]-3-methyl-L-valyl]-L-leucyl]amino]-4,4,4-trifluoro-butyraldehyde as a white solid; MS: m/e 945.4 [M+H].

EXAMPLE 36

In an analogous manner to Example 1, by replacing N-[(9-fluor-enyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 4-(4-methylphenyl)butyric acid there was obtained 2(RS)-[[N-[N-[N-[N-[N-[4-(4-methylphenyl)-butyryl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:6) as a white solid; MS: m/e 933.5 [M+H].

EXAMPLE 37

In analogous manner to Example 1, by replacing N-[(9-fluorenyl)methoxycarbonyl]-O-bebenzyl-α-glutamic acid with N-[(9-fluorenyl)methoxycarbonyl]-O-bet-butyl-L-α-glutamic acid and by replacing tert-butyl hydrogen succinate with 3-(4-methoxybenzoyl)propionic acid there was obtained 2(RS)-[N-[N-[N-[N-[3-(4-methylbenzoyl) propionyl-L-α-aspartyl]-L-α-glutamyl]-2-methyl-2-methyl-L-phenylalanyl]-3-methyl-L-valyl]-L-leucyl]amino]-4,4,4-trifluorobutyraldehyde (SEQ ID NO:7) as a white solid; MS: m/e 947.4 [M+H].

EXAMPLE 38

In an analogous manner to Example 1, by replacing N-[(9-fluorenyl)methoxycarbonyl]-O-bebenzyl-α-glutamic acid with N-[(9-fluorenyl)methoxycarbonyl-O-t-butyl-L-α-glutamic acid and by replacing tert-butyl hydrogen succinate with 2-(2-methoxyethoxy)ethoxy]acetic acid there was obtained 2(RS)-[[N-[N-[N-[N-[N-[2-[2-(2-methoxyethoxy) ethoxy-acetyl]-L-α-aspartyl]-L-α-glutamyl]-2-methyl-L-phenylalanyl]-3-methyl-L-valyl]-L-leucyl]amino]-4,4,4-trifluorobutyraldehyde as a white solid (SEQ ID NO:6) ; MS: m/e 933.4 [M+H].

EXAMPLE 39

In an analogous manner to Example 1, by replacing N-[(9-fluorenyl)methoxycarbonyl]-O-bebenzyl-α-glutamic acid with N-[(9-fluorenyl)methoxycarbonyl]-O-bet-butyl-L-α-glutamic acid and by replacing tert-butyl hydrogen succinate with 2-(4-oxo-2-thioxo-3-thiazolidinyl)acetic acid there was obtained 2(RS)-[[N-[N-[N-[N-[N-[2-(4-oxo-2-thioxo-3-thiazolidinyl)acetyl]-L-α-aspartyl]-L-α-glutamyl]- 2-methyl-L-phenylalanyl]-3-methyl-L-valyl]-L-leucyl]amino]-4,4,4-trifluorobutyraldehyde (SEQ ID NO:9) as a white solid; MS: m/e 946.3 [M+H].

EXAMPLE 40

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 3-(2-methyl-4-nitro-1-imidazolyl)propionic acid there was obtained 2(RS)-[[N-[N-[N-[N-[N-[3-(2-methyl-4-nitro-1-imidazolyl)propionyl]-L-α-aspartyl]-L-α-glutamyl]-2-methyl-L-phenylalanyl]-3-methyl-L-valyl]-L-leucyl]-4,4,4-trifluorobutyraldehyde (SEQ ID NO:10) as a white solid; MS: m/e 954.4 [M+H].

EXAMPLE 41

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 5-hexynoic acid there was obtained 2(RS)-[[N-[N-[N-[N-[N-(5-hexynoyl)-L-α-aspartyl]-L-α-glutamyl]-L-phenylanyl-3-methyl-L-valyl]-L-leucyl]amino]amino]-3,3,3-trifluorobutyraldhyde (SEQ ID NO:11) as a white solid; MS: m/e 867.4 [M+H].

EXAMPLE 42

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 6-quinolinecarboxylic acid there was obtained 2(RS)-[[N-[N-[N-[N-[N-[(6-quinolyl)carbonyl]-L-α-aspartyl]-L-α-glutamyl]-2-methyl-L-methyl-L-phenylalanyl]-3-methyl-L-valyl]-L-leucyl amino]-4,4,4-butyraldehyde as white solid; MS: m/e 928.4 [M+H].

EXAMPLE 43

In an analogous manner to Example 1, by replacing N-[(9-fluor-enyl)methoxycarbonyl]-O-benzyl-α-glutamic acid with N-[(9-fluorenyl)methoxycarbonyl[-O-t-butyl-L-α-glutamic acid and by replacing tert-butyl hydrogen succinate with 6-oxo-3-pyranylcarboxylic acid there was obtained 2(RS)-[[N-[N-[N-[N-[N-[(6-oxo-3-pyranyl)carbonyl]-L-α-aspartyl acid]-L-α-glutamyl]-2-methyl-L-phenylalanyl]-3-methyl-L-valyl]-L-leucyl]amino]-4,4,4-trifluorobutyraldehyde (SEQ ID NO:13) as a white solid; MS: m/e 895.4 [M+H].

EXAMPLE 44

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 2-(1,3-benzodioxol-5-yl)acetic acid there was obtained 2(RS)-[[N-[N-[N-[N-[N-[2-(1,3-benzodioxol-5-yl)-acetyl]-L-α-aspartyl]-L-α-glutamyl]-2-methyl-L-phenylalanyl-3-methyl-L-valyl -L-leucyl]amino -4,4,4-trifluorobutyraldehyde (SEQ ID NO:14) as a white solid; MS: m/e 935.4 [M+H].

EXAMPLE 45

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 5,6-dihydro-6,6-dimethyl-4-oxo-4H-pyran-2-ylcarboxylic acid there was obtained 2(RS)-[[N-[N-[N-[N-[N-[(5,6-dihydro-6,6-dimethyl-4-oxo-4H-pyran-2-yl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:15) as a white solid; MS: m/e 925.4 [M+H].

EXAMPLE 46

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 2-(2-naphthyl)acetic acid there was obtained 2(RS)-[[N-[N-[N-[N-[N-[2-(2-naphthyl)acetyl]-L-α-aspartyl]-L-α-glutamyl -2-methyl-L-phenylalanyl]-3-methyl-L-valyl-L-leucyl]amino]-4,4,4-trifluorobutyraldehyde (SEQ ID NO:16) as a white solid; MS: m/e 941.4 [M+H].

EXAMPLE 47

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 3-benzamidopropionic acid there was obtained 2(RS)-[[N-[N-[N-[N-[N-(3-benzamidopropionyl)-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:17) as a white solid; MS: m/e 948.4 [M+H].

EXAMPLE 48

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with,2,3,4-tetrahydro-2,4-dioxo-5-pyrimidinylcarboxylic acid there was obtained 2(RS)-[[N-[N-[N-[N-[N-(1,2,3,4-tetrahydro-2,4-dioxo-5-pyrimidinyl)carbonyl -L-α-glutamyl]-2-methyl-L-phenylalanyl]-3-methyl-L-valyl]-L-leucyl]amino]-4,4,4-trifluorobutyraldehyde (SEQ ID NO:18) as a white solid; MS: m/e 911.4 [M+H].

EXAMPLE 49

In an analogous manner to Example 1, by replacing N-[(9-fluorenyl)methoxycarbonyl]-O-benzyl-α-glutamic acid with N-[(9-fluorenyl)methoxycarbonyl]-O-t-butyl-L-α-glutamic acid and by replacing tert-butyl hydrogen succinate with 3-methyl-2-thenoic acid there was obtained 2(RS)-[[N-[N-[N-[N-[N-(3-methyl-2-thenoyl)-L-α-aspartyl]-α-glutamyl]-2-methyl-L-phenyl-alanyl]-3-methyl-L-valyl]-L-leucyl]amino-4,4,4-trifluorobutyraldehyde (SEQ ID NO:19) as a white solid; MS: m/e 897.4 [M+H].

EXAMPLE 50

In an analogous manner to Example 1, by replacing N-[(9-fluorenyl)methoxycarbonyl]-O-benzyl-α-glutamic acid with N-[(9-fluorenyl-methoxycarbonyl]-O-t-butyl-L-α-glutamic acid and by replacing tert-butyl hydrogen succinate with 2-cyclohexylacetic acid there was obtained 2(RS)-[[N-[N-[N-[N-[N-(2-cyclohexylacetyl)-L-α-aspartyl]-L-α-glutamyl]-2-methyl-L-phenylalanyl]-3-methyl-L-valyl]-L-leucyl]amino]-4,4,4-trifluorobutyraldehyde (SEQ ID NO:20) as a white solid; MS: m/e 897.5 [M+H].

EXAMPLE 51

In an analogous manner to Example 1, by replacing N-[(9-fluorenyl)methoxycarbonyl]-O-benzyl-α-glutamic acid with N-[(9-fluorenyl)methoxycarbonyl]-O-butyl-L-α-glutamic acid and by replacing tert-butyl hydrogen succinate with 2(RS)-(4-nitrophenyl)propionic acid there was obtained 2(RS)-[[N-[N-[N-[N-[N-[2(RS)-(4-nitrophenyl)propionyl]-L-α-aspartyl]-L-α-glutamyl -2-methyl-L-phenylalanyl]-3-methyl-L-valyl-L-leucyl]amino]-4,4,4-trifluorobutyraldehyde (SEQ ID NO:21) as a white solid; MS: m/e 950.3 [M+H].

EXAMPLE 52

4 g of 0.25 mmol/g 5-[2-[1(RS)-[[N-[9-fluorenyl)methoxycarbonyl]-L-leucyl]amino]propyl]-4(RS),5,5-trimethyl-1,3,2-dioxoborolan-4-yl]-3(RS)-methyl-N-[α(RS)-(4-methylphenyl)benzyl]valeramide-polystyrene conjugate were swollen in dimethylformamide for 20 minutes and then suspended and agitated in dimethylformamide/piperidine (4:1). After 5 minutes the resin was drained and then re-suspended in and agitated with dimethylformamide/piperidine (4:1) for a further 5 minutes. The resin was then drained and washed five times with dimethylformamide.

The resin was suspended in a solution of 2.1 g (6 mmol) of N-[(9-fluorenyl)methoxycarbonyl]-3-methyl-L-valine in dimethylformamide and then a mixture of 1.9 g of 2-(1H-benzotriazol-1-yl)-1,1,3,3-tetramethyluronium tetrafluoroborate and 1.3 ml of N-methylmorpholine dissolved in dimethyl-formamide was added. After agitating for 40 minutes the resin was drained and washed five times with dimethylformamide.

The resin was suspended in and agitated with dimethylfomamide/piperidine (4.1). After 5 minutes the resin was drained and resuspended in and agitated with dimethylformamide/piperidine (4:1) for a further 5 minutes. Then, the resin was drained and washed five times with dimethylformamide.

The resin was resuspended in a solution of 2.4 g (6 mmol) of N-[(9-fluorenyl)methoxycarbonyl]-3-(2-methylphenyl)-L-alanine in dimethylformamide and then a mixture of 1.9 g of 2-(2-1H-benzotriazol-1-yl)-1,1,3,3-tetramethyluronium tetrafluoroborate and 1.3 ml of N-morpholine dissolved in dimethylformamide was added. After agitating for 40 minutes the resin was drained and washed five times with dimethylformamide.

40 mg of the resin obtained according to the preceding paragraph were suspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with dimethylformamide.

The resin was suspended in 0.5 ml of a 0.2M solution of N-[(9-fluorenyl)methoxycarbonyl]-L-glutamic acid γ-benzyl ester in dimethyl sulphoxide and then 0.5 ml of a mixture of 0.2M 2-(1H-benzotriazol-1-yl)-1,1,3,3-tetramethyluronium tetrafluoroborate and 0.4M N-methylmorpholine in dimethylformamide was added. After agitating for 1 hour the resin was drained and washed five times with 1 ml of dimethylformamide.

The resin was resuspended in and agitated with 0.7 ml of dimethyformamide/piperidine (4:1). After 5 minutes the resin was drained and resuspended in and agitated with dimethylformamide/piperidine (4:1) for a further 5 minutes. Then, the residue was drained and washed five times with 1 ml of dimethylformamide.

The resin was suspended in 0.5 ml of a 0.2M solution of 1-(2,4-dinitrophenyl)-N-[(9-fluorenyl)methoxycarbonyl]-L-histidine in dimethyl sulphoxide and then 0.5 ml of a mixture of 0.2M 2-(1H-benzotriazol-1-yl)-1,1,3,3-tetramethyluronium tetrafluoroborate and 0.4M N-methylmorpholine dissolved in dimethylformamide was added. After agitating for 1 hour the resin was drained and washed five times with 1 ml of dimethylformamide The resin was resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the residue was drained and washed five times with 1 ml of dimethylformamide.

The resin was suspended in 0.5 ml of a 0.2M solution of acetic anhydride in dimethylformamide and then 0.5 ml of a mixture of 0.2M 2-(1H-benzotriazol-1-yl)-1,1,3,3-tetramethyluronium tetrafluoroborate and 0.4M N-methylmorpholine dissolved in dimethylformamide was added. After agitating for 1 hour the resin was drained and washed five times with 1 ml of dimethylformamide and then twice with 1 ml of dichloromethane.

0.2 ml of dichloromethane was added to the residue which was then treated with 0.7 ml of trifluoroacetic acid/water (19:1) and agitated for 90 minutes. The residue was filtered off and washed with 0.7 ml of trifluoroacetic acid/water (19:1). The combined trifluoroacetic acid/water solutions were then evaporated in a vacuum centrifuge and the residue was suspended in acetonitrile/water and freeze dried. There were obtained 8 mg of 1(RS)-[N-[N-[N-[N-acetyl-1-(2,4-dinitrophenyl)-L-histidyl]O-benzyl-L-α-glutamyl]-2-methyl-L-phenylalanyl]-3-methyl-L-valyl]-L-leucyl]amino] propylboronic acid as a white solid; MS: m/e 888.5 [M+H-1671]$^+$.

The starting material was prepared as follows:
i) 25 ml of isobutylene were condensed at −78° C. and added to a mixture of 19.4 g (114 mmol) of 3(RS),7-dimethyl-6-octenoic acid and 1 ml of concentrated sulphuric acid in 25 ml of dichloromethane. The mixture was stirred for 24 hours under a dry ice condenser. A further 20 ml of isobutylene were added and the mixture was stirred for 24 hours under a dry ice condenser. The mixture was diluted with dichloromethane, washed with saturated sodium bicarbonate solution, dried over anhydrous magnesium sulphate and evaporated under a vacuum. The resulting oil was purified by chromatography on silica gel using ethyl acetate/hexane (1:9) for the elution. There were obtained 20.8 g of tert-butyl 3(RS),7-dimethyl-6-octenoate as a colourless oil. $^1$H NMR (250 MHz, CDCl$_3$)δ: 0.9 (d, 3H), 1.1–1.3 (m,3H), 1.4 (s, 9H), 1.6 (s, 3H), 1.65, (s, 3H), 1.8–2.2 (br m, 4H), 5.05, (m, 1H).

ii) 1.5 g (6.64 mmol) of tert-butyl 3(RS),7-dimethyl-6-octenate were dissolved in a mixture of 10 ml of acetone, 2 ml of water and 2 ml of glacial acetic acid. 2 g (12.6 mmol) of potassium permanganate were added and the resulting mixture was stirred at 30° C. for 2 hours. 22 ml of 2M sulphuric acid and 0.8 g (11.3 mmol) of sodium nitrite were added and the organic phase was separated. The aqueous phase was extracted with dichloromethane and the combined organic phases were washed with water, dried over magnesium sulphate and evaporated under a vacuum to give 1.55 g of tert-butyl 7-hydroxy-3(RS),7-dimethyl-6-oxo-octenoate as a clear oil; MS: m/e 259 [M+H]+.

iii) 0.25 g (0.97 mmol) of tert-butyl 7-hydroxy-3(RS),7-dimethyl-6-oxo-octenoate was dissolved in 3 ml of diethyl ether at 0° C. under a nitrogen atmosphere. 0.36 ml (1.1 mmol) of 3M methylmagnesium bromide in diethyl ether was added dropwise and the resulting solution was stirred at 0° C. for 2 hours, refluxed for 6 hours and then stirred at room temperature for 16 hours. The solution was diluted with ethyl acetate and then extracted with 2M hydrochloric acid and saturated sodium chloride solution. The organic phase was dried over anhydrous sodium sulphate and evaporated under a vacuum. The resulting oil was purified by chromatography on silica gel using ethyl acetate/hexane (1:2) for the elution. There were obtained 118 mg of tert-butyl 6(RS),7-dihydroxy-3(RS),6,7-trimethyl-6-octenoate as a clear oil; MS: m/e 275 [M+H]$^+$.

iv) 0.64 g (2.3 mmol) of tert-butyl 6(RS),7-dihydroxy-3-(RS),6,7-trimethyl-6-octenoate was stirred in 3 ml of tetrahydrofuran with 0.5 g (2.5 mmol) of dichloromethyl diisopropoxyborane at room temperature for 16 hours. The resulting mixture was evaporated and the residue was co-evaporated with toluene to give 0.86 g of tert-butyl 5-[2-(dichloromethyl)-4(RS),5,5-trimethyl-1,3,2-dioxaborolan-4-yl]-3(RS)-methylvalerate as an oil which was used in the next step without further purification.

v) 0.86 g (2.3 mmol) of tert-butyl 5-[2-(dichloromethyl)-4(RS),5,5-trimethyl-1,3,2-dioxaborolan-4-yl]-3(RS)-methylvalerate was dissolved in 5 ml of tetrahydrofuran and the solution was cooled to −78° C. under a nitrogen atmosphere. 2.6 ml (2.6 mmol) of 1M ethylmagnesium bromide in tetrahydrofuran were added dropwise, the resulting solution was stirred for 16 hours while slowly warming to room temperature and then diluted with ethyl acetate and extracted with 2M hydrochloric acid and brine. The organic phase was dried over sodium sulphate and then evporated under a vacuum to give 0.83 g of tert-butyl 5-[2-(1(RS)-chloropropyl)-4(RS),5,5-trimethyl-1,3,2-dioxaborolan-4-yl]-3(RS)-methylvalerate as an oil which was used in the next step without purification.

vi) 0.82 g (2.27 mmol) of tert-butyl 5-[2-(1(RS)-chloropropyl)-4(RS),5,5-trimethyl-1,3,2-dioxaborolan-4-yl]-3(RS)-methylvalerate was dissolved in 10 ml of tetrahydrofuran and then cooled to −78° C. under a nitrogen atmosphere. 2.3 ml (2.3 mmol) of 1M lithium bis(trimethylsilyl)amide in tetrahydrofuran were added dropwise. The solution was then stirred overnight while slowly warming to room temperature. The solvent was removed by evaporation and the residue was taken up in diethyl ether. Insoluble material was removed by filtration and the filtrate was cooled to 0° C. 0.52 ml (6.8 mmol) of trifluoroacetic acid was added and the solution was stirred at 0° C. for 30 minutes. The solution was evaporated and the residue was co-evaporated with toluene to give 1 g of tert-butyl 5-[2-(1(RS)-aminopropyl)-4(RS), 5,5-trimethyl-1,3,2-dioxaborolan-4-yl]-3(RS)-methylvalerate as an oil which was used in the next step without purification.

vii) 0.5 g (1.42 mmol) of N-[(9-fluorenyl)methoxycarbonyl]-L-leucine was dissolved in 7 ml of dichlormethane. 0.6 ml (5. mmol) of N-methylmorpholine was added and the solution was cooled to −10° C. under a nitrogen atmosphere. 0.22 ml (1.7 mmol) of isobutyl chloroformate was added and the solution was stirred for 7 minutes at −10° C. 1 g (2.13 mmol) of tert-butyl 5-[2-(1(RS)-aminopropyl)-4(RS),5,5-trimethyl-1,3,2-dioxaborolan-4-yl]-3(RS)-methylvalerate was added and the mixture was stirred at room temperature for 16 hours, then diluted with dichloromethane and extracted with 2M hydrochloric acid. The organic phase was extracted with 2M hydrochloric acid and saturated sodium hydrogen carbonate solution and then dried over anhydrous magnesium sulphate. After evaporation the residue was purified by chromatography on silica gel using ethyl acetate/hexane (1:2) for the elution. There was obtained 0.56 g of tert-butyl 5-[2-[1(RS)-[[N-[(9-fluorenyl)methoxycarbonyl]-L-leucyl]amino]amino]propyl]-4(RS),5,5-trimethyl-1,3,2-dioxaborolan-4-yl]-3(RS)-methylvalerate as an oil; MS: m/e 677 [M+H]$^+$.

viii) 50 mg (0.074 mmol) of tert-butyl 5-[2-[1(RS)-[[N-[(9-fluorenyl)methoxycarbonyl]-L-leucyl]amino]propyl]-4(RS),5,5-trimethyl-1,3,2-dioxaborolan-4-yl]-3(RS)-methylvalerate were dissolved in 1 ml of trifluoroacetic acid and 1 ml of dichloromethane. The solution was stirred at room temperature for 15 minutes and then evaporated under a vacuum. The residue was co-evaporated with toluene to give 46 mg of 5-[2-[1(RS)-[[N-[(9-fluorenyl)methoxycarbonyl]-L-leucyl]amino]propyl]-4(RS),5,5-trimethyl-1,3,2-dioxaborolan-4-yl]-3(RS)-methylvaleric acid as an oil; MS: m/e 621 [M+H]$^+$.

ix) 5 g (5.25 mmol) of 4-methylbenzhydrylamine resin were swollen in dimethylformamide and excess solvent was drained from the resin. The resin was then resuspended in dimethylformamide containing 3.4 g (5.48 mmol) of 5-[2-[1(RS)-[[N-[(9-fluorenyl)methoxycarbonyl]-L-leucyl]amino]propyl]-4(RS),5,5-trimethyl-1,3,2-dioxaborolan-4-yl]-3(RS)-methylvaleric acid and 3 g (8.2 mmol) of 2-(1H-benzotriazol-1-yl)-1,1,3,3-tetramethyluronium hexafluorophosphate. Thereto were added 3.0 ml (16.5 mmol) of diisopropylamine. The resulting mixture was agitated for 100 minutes and the resin was then drained and washed three times with dimethylformamide. The resin was then resuspended in dimethylformamide containing 5 ml (54.8 mmol) of acetic anhydride and 11.5 ml (110 mmol) of N-methylmorpholine. The mixture was agitated for 30 minutes and the resin was then drained. The resin was then resuspended in dimethylformamide containing 5 ml (54.8 mmol) of acetic anhydride and 11.5 ml (110 mmol) of N-methylmorpholine. The mixture was agitated for 30 minutes and the resin was then drained and washed three times with dimethylformamide, twice with ethyl acetate, twice with dichloromethane and twice with diethyl ether and then dried under a vacuum. After drying there was obtained 6 g of 5-[2-[1(RS)-[[N-[(9-fluorenyl)methoxycarbonyl]-L-leucyl]amino]propyl]-4-(RS),5,5-trimethyl-1,3 ,2-dioxoborolan-4-yl]-3(RS)-methyl-N-(RS)-(4-methylphenyl)-benzyl]valeramide-polystyrene conjugate as a pale brown solid (0.25 mmol/g loading estimated by quantitation of dibenzofulvene at 301 nM).

EXAMPLE 53

In an analogous manner to that described in Example 52, by replacing N-[(9-fluorenyl)methoxycarbonyl]-L-glutamic acid γ-benzyl ester with N-[(9-fluorenyl)methoxycarbonyl]-N6-(p-toluenesulfonyl)-L-arginine there was obtained 1(RS)-[[N-[N-[N-[N2-[N-acetyl-1-(2,4-dinitrophenyl)-L-histidyl]-N6-(p-toluenesulfonyl)-L-arginyl]-2-methyl-L-phenylalanyl]-3-methyl-L-valyl]-L-leucyl]amino] propylboronic acid as a white solid; MS: m/e 980.3 [M+H−1671]$^+$.

EXAMPLE 54

In an analogous manner to that described in Example 52, by replacing N-[(9-fluorenyl)methoxycarbonyl]-L-glutamic acid γ-benzyl ester with N-[(9-fluorenyl)methoxycarbonyl]-O-benzyl-D-tyrosine there was obtained 1(RS)-[[N-[N-5 [N-[N-[N-acetyl-1-(2,4-dinitrophenyl)-L-histidyl]-O-benzyl-D-tyrosyl]-2-methyl-L-phenylalanyl]-3-methyl-L-valyl]-L-leucyl]amino]propylboronic acid as a white solid; MS: m/e 905.5 [M+H−H$_2$O−1671]$^+$.

EXAMPLE 55

In an analogous manner to that described in Example 52, by replacing N-[(9-fluorenyl)methoxycarbonyl]-L-glutamic acid γ-benzyl ester with N-[(9-fluorenyl)methoxycarbonyl]-4-nitro-D-phenylalanine there was obtained 1(RS)-[[N-[N-[N-[N-[N-acetyl-1-(2 ,4-dinitrophenyl)-L-histidyl]-4-nitro-D-phenylalanyl]-2-methyl-L-phenylalanyl]-3-methyl-L-valyl]-L-leucyl]amino]propylboronic acid as a white solid; MS: m/e 844.4 [M+H−H$_2$O−167]$^+$.

EXAMPLE 56

In an analogous manner to that described in Example 52, by replacing N-[(9-fluorenyl)methoxycarbonyl]-L-glutamic acid γ-benzyl ester with N-[(9-20 fluorenyl)methoxycarbonyl]-O-benzyl-D-serine there was obtained 1(RS)-[[N-[N-[N-[N-[N-acetyl-1-(2,4-dinitrophenyl)-L-histidyl]-O-benzyl-D-seryl]-2-methyl-L-phenylalanyl]-3-methyl-L-valyl]-L-leucyl]amino]propylboronic acid as a white solid; MS: m/e 829.5 [M+H−H$_2$O−167]$^+$.

EXAMPLE 57

In an analogous manner to that described in Example 52, by replacing N-[(9-fluorenyl)methoxycarbonyl]-L-glutamic acid γ-benzyl ester with N-[(9-fluorenyl)methoxycarbonyl-L-2-cyclohexylglycine there was obtained 1(RS)-[[N-[N-[N-[N-[N-acetyl- 1-(2,4-dinitrophenyl)-L-histidyl]-L-2-cyclohexylglycyl]-2-methyl-L-phenylalanyl]-3-methyl-L-valyl]-L-leucyl]amino]propylboronic acid; MS: m/e 751.5 [M+H−H$_2$O−1671]$^+$.

EXAMPLE 58

In an analogous manner to that described in Example 52, by replacing N-[(9-fluorenyl)methoxycarbonyl]-L-glutamic acid γ-benzyl ester with N-[(9-fluorenyl)methoxycarbonyl]-D-2-phenylglycine there was obtained 1(RS)-[[N-[N-N-[N-[N-acetyl-1-(2,4-dinitrophenyl)-L-histidyl]-D-2-phenylglycyl]-2-methyl-L-10 phenylalanyl]-3-methyl-L-valyl]-L-leucyl]amino]propylboronic acid; MS: m/e 791.5 [M+H−H$_2$O−167]$^+$.

EXAMPLE 59

In an analogous manner to that described in Example 52, by replacing 1-(2,4-dinitrophenyl)-N-[(9-fluorenyl)methoxycarbonyl]-L-histidine with N-[(9-fluorenyl)methoxycarbonyl]-O-benzyl-L-serine and by replacing N-[(9-fluorenyl)methoxycarbonyl]-L-glutamic acid γ-benzyl ester with N-[(9-fluorenyl)methoxycarbonyl]-N6-nitro-L-arginine there was obtained 1(RS)-[[N-[N-[N-[N2-[N-acetyl-O-benzyl-L-seryl]-N6-nitro-L-arginyl]-2-methyl-L-phenylalanyl]-3-methyl-L-valyl]-L-leucyl]amino] propylboronic acid; MS: m/e 893.5 [M+H−H$_2$O]$^+$.

EXAMPLE 60

In an analogous manner to that described in Example 52, by replacing 1-(2,4-dinitrophenyl)-N-[(9-fluorenyl) methoxycarbonyl]-L-histidine with N-[(9-fluorenyl) methoxycarbonyl]-O-benzyl-L-serine and by replacing N-[(9-fluorenyl)methoxycarbonyl]-L-glutamic acid γ-benzyl ester with N-[(9-fluorenyl)methoxycarbonyl]-S-benzyl-L-cysteine there was obtained 1(RS)-[[N-[N-N-[N-(N-acetyl-O-benzyl-L-seryl)-S-benzyl-L-cysteinyl]-2-methyl-L-henylalanyl]-3-methyl-L-valyl]-L-leucyl]amino] propylboronic acid; MS: m/e 885.5 M+H−H$_2$O]$^+$.

EXAMPLE 61

In an analogous manner to that described in Example 52, by replacing 1-2,4-dinitrophenyl)-N-[(9-fluorenyl)methoxy] carbonyl]-L-histidine with N-[(9-luorenyl) methoxycarbonyl]-O-benzyl-L-serine and by replacing N-[(9-luorenyl)methoxycarbonyl]-L-glutamic acid γ-benzyl ester with 1-tert-butoxycarbonyl-N-[(9-fluorenyl) methoxycarbonyl]-D-tryptophan there was obtained 1(RS)-[[N-[N-[N-[N-(N-acetyl-O-benzyl-L-seryl)-D-tryptophyl]-2-methyl-L-henylalanyl]-3-methyl-L-valyl]-L-leucyl] amino]propylboronic acid; MS: m/e 875.8 [M+H−H$_2$O]$^+$.

EXAMPLE 62

In an analogous manner to that described in Example 52, by replacing 1-(2,4-dinitrophenyl)-N-[(9-fluorenylmethoxycarbonyl -L-histidine with N-[(9-fluorenyl)methoxycarbonyl]-O-benzyl-L-serine and by replacing N-[(9-fluorenyl)methoxycarbonyl]-L-glutamic acid γ-benzyl ester with N-[(9-fluorenyl)methoxycarbonyl]-D-valine there was obtained 1(RS)-[[N-[N-[N-[N-(N-acetyl-O-benzyl-L-seryl)-D-valyl]-2-methyl-L-phenylalanyl]-3-methyl-L-valyl]-L-leucyl]amino] propylboronic acid; MS: m/e 791.5 [M+H−H$_2$O]$^+$.

EXAMPLE 63

In an analogous manner to that described in Example 52, by replacing 1-(2,4-dinitrophenyl)-N-[(9-fluorenyl) methoxycarbonyl]-L-histidine with N-[(9-fluorenyl) methoxycarbonyl]-S,S-dioxo-L-methionine and by replacing N-[(9-fluorenyl)methoxycarbonyl]-L-glutamic acid γ-benzyl ester with N-[(9-fluorenyl)methoxycarbonyl]-N6-nitro-L-arginine there was obtained 1(RS)-[[N-[N-[N-[N2-(N-acetyl-S,S-dioxo-L-methionyl)-N 6-nitro-L-arginyl -2-methyl-L-phenylalanyl]-3-methyl-L-valyl]-L-leucyl] amino]propylboronic acid; MS: m/e 879.5 [M+H−H$_2$O]$^+$.

EXAMPLE 64

In an analogous manner to that described in Example 52, by replacing 1-(2,4-dinitrophenyl)-N-[(9-fluorenyl) methoxycarbonyl]-L-histidine with N-[(9-fluorenyl) methoxycarbonyl]-O-tert-butyl-L-α-aspartic acid and by replacing N-[(9-fluorenyl)methoxycarbonyl]-L-glutamic acid γ-benzyl ester with N-[(9-fluorenyl)methoxycarbonyl]-S,S-dioxo-L-methionine there was obtained 1(RS)-[[N-[N-[N-[N-(N-acetyl-L-α-aspartyl)-S,S-dioxo-L-methionyl]-2-methyl-L-phenylalanyl]-3-methyl-L-valyl]-L-leucyl]amino] propylboronic acid (SEQ ID NO:3) as a white solid; MS: m/e 793.4 [M+H−H$_2$O]$^+$.

EXAMPLE 65

In an analogous manner to that described in Example 52, by replacing 1-(2,4-dinitrophenyl)-N-[(9-fluorenylmethoxycarbonyl]-L-histidine with N-[(9-fluorenyl)methoxycarbonyl]-O-tert-butyl-L-α-aspartic acid and by replacing N-(9-fluorenyl)methoxycarbonyl]-L-glutamic acid γ-benzyl ester with N-[(9-fluorenyl)methoxycarbonyl]-S-[(acetamido)methyl]-L-cysteine there was obtained 1(RS)-[[N-[N-[N-[N-(N-acetyl-L-α-aspartyl)-S-[(acetamido)methyl]-L-cysteinyl]-2-methyl-L-phenylalanyl]-3-methyl-L-valyl]-L-leucyl]amino]propylboronic acid (SEQ ID NO:4) as a white solid; MS: m/e 804.4 [M+H–H$_2$O]$^+$.

EXAMPLE 66

4 g of 0.25 mmol/g 5-[2-[1(RS)-[[N-[(9-fluorenyl)methoxycarbonyl]-L-leucyl]amino]propyl]-4(RS),5,5-trimethyl-1,3,2-dioxoborolan-4-yl]-3(RS)-methyl-N-[α(RS)-(4-methylphenyl)benzyl]valeramide-polystyrene conjugate (prepared as described in Example 52) were swollen in dimethylformamide for 20 minutes and then suspended and agitated in dimethylformamide/piperidine (4:1). After 5 minutes the resin was drained and then resuspended in and agitated with dimethylformamide/piperidine (4:1) for a further 5 minutes. The resin was then drained and washed five times with dimethylformamide.

The resin was then suspended in a solution of 2.1 g (6 mmol) of N-[(9-fluorenyl)methoxycarbonyl]-3-methyl-L-valine in dimethylformamide and then a mixture of 1.9 g of 2-(1H-benzotriazol-1-yl)-1,1,3,3-tetramethyluronium tetrafluoraborate and 1.3 ml (0.12 mmol) of N-methylmorpholine dissolved in dimethylformamide was added. After agitating for 40 minutes the resin was drained and washed five times with dimethylformamide.

The resin was resuspended in and agitated with dimethylformamide/piperidine (4:1). After 5 minutes the resin was drained and resuspended in and agitated with dimethylformamide/piperidine(4:1) for a further 5 minutes. Then, the resin was drained and washed five times with 1.5 ml of dimethylformamide.

The resin was then suspended in a solution of 2.4 g (6 mmol) of N-[(9-fluorenyl)methoxycarbonyl]-3-(2-methylphenyl)-L-alanine in dimethylformamide and then a mixture of 1.9 g of 2-(1H-benzotriazol-1-yl)-1,1,3,3-tetramethyl-uronium tetrafluoraborate and 1.3 g of N-methylmorpholine dissolved in dimethylformamide was added. After agitating for 40 minutes the resin was drained and washed five times with dimethylformamide.

40 mg of this resin were resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with dimethylformamide.

The resin was then suspended in 0.5 ml of a 0.2M solution of N-[(9-fluorenyl)methoxycarbonyl]-O-tert-butyl-L-α-glutamic acid in dimethyl sulphoxide and then 0.5 ml of a mixture of 0.2M 2-(1H-benzotriazol-1-yl)-1,1,3,3-tetramethyluronium tetrafluoroborate and 0.4M N-methylmorpholine in dimethylformamide was added. After agitating for 1 hour the resin was drained and washed five times with 1 ml of dimethylformamide.

The resin were resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The resin was then suspended in 0.5 ml of a 0.2M solution of N-[(9-fluorenyl)methoxycarbonyl]-O-tert-butyl-L-α-aspartic acid in dimethyl sulphoxide and then 0.5 ml of a mixture of 0.2M 2-(1H-benzotriazol-1-yl)-1,1,3,3-tetramethyl-uronium tetrafluoroborate and 0.4M N-methylmorpholine in dimethylformamide was added. After agitating for 1 hour the resin was drained and washed five times with 1 ml of dimethylformamide.

The resin were resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The resin was suspended in 0.5 ml of a 0.2M solution of coumalic acid in dimethylformamide and then 0.5 ml of a mixture of 0.2M 2-(1H-benzotriazol-1-yl)-1,1,3,3-tetramethyluronium tetrafluoroborate and 0.4M N-methylmorpholine in dimethylformamide was added. After agitating for 1 hour the resin was drained and washed five times with 1 ml of dimethylformamide and then twice with 1 ml of dichloromethane. 0.2 ml of dichloromethane was added to the resin which was then treated with 0.7 ml of trifluoroacetic acid/water (19:1) and then agitated for 90 minutes. It was then filtered off and washed with 0.7 ml of trifluoroacetic acid/water (19:1). The combined trifluoroacetic acid/water mixtures were then evaporated in a vacuum centrifuge and the residue was suspended in acetonitrile/water (1:1) and freeze dried. There were obtained 7 mg of 1(RS)-[[N-[N-[N-[N-[N-(6-oxo-6H-pyran-3-yl)carbonyl]-L-α-aspartyl]-L-α-glutamyl]-2-methyl-L-phenylalanyl]-3-methyl-L-valyl]-L-leucyl]amino]propylboronic acid (SEQ ID NO:22); MS: m/e 839.4 [M+H–H$_2$O]$^+$.

EXAMPLE 67

In an analogous manner to Example 66, by replacing coumalic acid with 4-acetamidobutanoic acid there was obtained 1(RS)-[[N-[N-[N-[N-(4-acetamidobutyryl)-L-α-aspartyl]-L-α-glutamyl]-2-methyl-L-phenylalanyl]-3-methyl-L-valyl]-L-leucyl]amino]propylboronic acid (SEQ ID NO:23); MS: m/e 844.5 [M+H–H$_2$O]$^+$.

EXAMPLE 68

In an analogous manner to Example 66, by replacing coumalic acid with acetoxy-acetic acid there was obtained 1(RS)-[[N-[N-[N-[N-(2-acetoxyacetyl)-L-α-aspartyl]-L-α-glutamyl]-2-methyl-L-phenylalanyl]-3-methyl-L-valyl]-L-leucyl]amino]propylboronic acid (SEQ ID NO:24); MS: m/e 817.5 [M+H–H$_2$O]$^+$.

The following Examples illustrate pharmaceutical preparations containing compounds of formula I:

EXAMPLE A

Tablets containing the following ingredients may be produced in a conventional manner:

| Ingredient | Per tablet |
|---|---|
| Compound of formula 1 | 10.0 mg |
| Lactose | 125.0 mg |
| Corn starch | 75.0 mg |
| Talc | 4.0 mg |
| Magnesium stearate | 1.0 mg |
| Total weight | 215.0 mg |

EXAMPLE B

Capsules containing the following ingredients may be produced in a conventional manner:

| Ingredients | Per capsule |
|---|---|
| Compound of formula 1 | 10.0 mg |
| Lactose | 165.0 mg |
| Corn starch | 20.0 mg |
| Talc | 5.0 mg |
| Capsule fill weight | 200.0 mg |

What is claimed is:

1. A compound having the formula

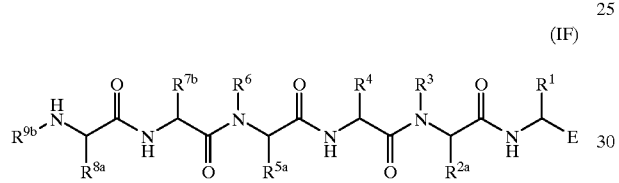

(IF)

wherein:

E represents —CHO or —B(OH)$_2$;

$R^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

$R^{2a}$ is selected from the group consisting of lower alkyl, hydroxy-lower alkyl, carboxy-lower alkyl, aryl-lower alkyl, aminocarbonyl-lower alkyl and lower cycloalkyl-lower alkyl;

$R^3$ represents hydrogen or lower alkyl; or $R^{2a}$ and $R^3$ together represent di-or trimethylene optionally substituted by hydroxy;

$R^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

$R^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

$R^6$ represents hydrogen or lower alkyl;

$R^{7b}$ is selected from the group consisting of aryl-lower alkylthio-lower alkyl, aryl-lower alkoxy-aryl-lower alkyl, aryl-lower alkoxycarbonyl-lower alkyl, aryl-lower alkylcarbonyl-lower alkyl, nitroguanidino-lower alkyl, arylsulfonyl-guanidino-lower alkyl, lower alkylsulfonyl-lower alkyl, acetamidomethylthio-lower alkyl, aryl and heteroaryl-lower alkyl;

$R^{8a}$ is selected from the group consisting of lower alkyl, hydroxy-lower alkyl, carboxy-lower alkyl and aryl-lower alkyl; and $R^{9b}$ is selected from the group consisting of aryl-lower alkylcarbonyl, heteroaryl-lower alkylcarbonyl, arylaminocarbonyl-lower alkylcarbonyl, heteroarylthio-lower alkylcarbonyl, heteroarylcarbonyl, hydroxyfluorenylcarbonyl, heteroarylcarbonyl-lower alkylcarbonyl, lower alkoxy-lower alkylcarbonyl, aryl-carbonyl-lower alkylcarbonyl, lower alkoxy-lower alkoxy-lower alkoxy-lower alkylcarbonyl, arylcarbonylamino-lower alkylcarbonyl, lower cycloalkyl-lower alkylcarbonyl, lower alkylcarbonyl-lower cycloalkyl-lower alkylcarbonyl, lower alkylcarbonylamino-lower alkylcarbonyl, heterocyclylcarbonyl, lower alkylcarbonyloxy-lower alkylcarbonyl, lower alkoxycarbonyl-lower alkylcarbonyl, aryloxy-lower alkylcarbonyl, lower alkynylcarbonyl and lower cycloalkylcarbonyl.

2. A compound of claim 1 wherein $R^1$ is lower alkyl or halo-lower alkyl; $R^2$ is lower alkyl; $R^3$ is hydrogen; $R^4$ is lower alkyl; $R^{5a}$ is aryl-lower alkyl; $R^6$ is hydrogen; $R^{8a}$ is carboxy-lower alkyl, hydroxy-lower alkyl or aryl-lower alkyl; and $R^{9b}$ is heteroarylcarbonyl, hydroxyfluorenylcarbonyl, heterocyclylcarbonyl, heteroarylcarbonyl-lower alkylcarbonyl, heteroaryl-lower alkylcarbonyl or aryl-lower alkylcarbonyl.

3. A compound of claim 2 which is 2(RS)-[[N-[N-[N-[N-[N-[(9-hydroxy-9-fluorenyl)carbonyl-L-seryl]-O-benzyl-D-seryl]-2-methyl-L-phenylalanyl]-3-methyl-L-valyl]-L-leucyl]amino]-4,4,4-trifluorobutyraldehyde.

4. A compound of the formula

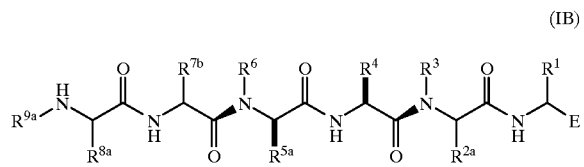

(IB)

wherein

E is —CHO or —B(OH)$_2$;

$R^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

$R^{2a}$ is selected from the group consisting of lower alkyl, hydroxy-lower alkyl, carboxy-lower alkyl, aryl-lower alkyl, aminocarbonyl-lower alkyl and lower cycloalkyl-lower alkyl;

$R^3$ is hydrogen or lower alkyl; or taken together with $R^{2a}$ form di-or trimethylene optionally substituted by hydroxy;

$R^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

$R^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

$R^6$ is hydrogen or lower alkyl;

$R^{7b}$ is selected from the group consisting of aryl-lower alkylthio-lower alkyl, aryl-lower alkoxy-aryl-lower alkyl, aryl-lower alkoxycarbonyl-lower alkyl, aryl-lower alkylcarbonyl-lower alkyl, nitroguanidino-lower alkyl, arylsulfonyl-guanidino-lower alkyl, lower alkylsulfonyl-lower alkyl, acetamidomethylthio-lower alkyl, aryl and heteroaryl-lower alkyl;

$R^{8a}$ is selected from the group consisting of lower alkyl, hydroxy-lower alkyl, carboxy-lower alkyl and aryl-lower alkyl; and $R^{9a}$ is selected from the group consisting of lower alkylcarbonyl, carboxy-lower alkyl-carbonyl, arylcarbonyl, lower alkylsulfonyl, arylsulfonyl, lower alkoxycarbonyl and aryl-lower alkoxycarbonyl;

or basic salts of acidic compounds thereof.

5. The compound of claim 4 wherein said compound is selected from the group consisting of:

2(RS)-[[N-[N-[N-[N-[N-(3-carboxypropionyl)-L-α-aspartyl]-O-benzyl-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-N6-nitro-L-arginyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-S-(acetamidomethyl)-L-cysteinyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-S-benzyl-L-cysteinyl]-2-methyl-L-phenylalanyl]-3-methyl-L-valyl]-L-leucyl]amino ]-4,4,4-trifluorobutyraldehyde;

2(RS)-[[N-[N-[-[N-[N-(3-carboxypropionyl)-L-α-aspartyl]-3-(3-thenyl)-D-alanyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-D-tryptophyl]-2-methyl-L-phenylalanyl]-3-methyl-L-valyl]-L-leucyl]amino]-4,4,4-trifluorobutyraldehyde;

2(RS)-[[N-[N-[-N-[N-(3-carboxypropionyl)-L-α-aspartyl]-O-benzyl-D-tyrosyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-S-(4-methoxybenzyl)-D-cysteinyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-O-benzyl-D-threonyl]-2-methyl-L-phenylalanyl]-3-methyl-L-valyl]-L-leucyl]amino]-4,4,4-trifluorobutyraldehyde;

2(RS)-[[N-[N-[N-[N-[N-(4-chloro-3-sulphamoylbenzoyl)-L-seryl]]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(4-acetamidobenzoyl)-L-seryl]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(3-hydroxy-4,5-dimethoxybenzoyl)-L-seryl)]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-[N-(2-ethylbutyryl)-L-seryl)]-O-benzyl-D-seryl]-2-methyl-L-phenylalanyl]-3-methyl-L-valyl]-L-leucyl]amino]-4,4,4-trifluorobutyraldehyde;

2(RS)-[[N-[N-[N-[N-(N-acetyl-L-α-aspartyl)-S,S-dioxo-L-methionyl]-2-methyl-L-phenylalanyl]-3-methyl-L-valyl]-L-leucyl]amino]propylboronic acid; and 1(RS)-[[N-[N-[N-[N-(N-acetyl-L-α-aspartyl)-S-[(acetamido)methyl]-L-cysteinyl]-2-methyl-L-phenylalanyl]-3-methyl-L-valyl]-L-leucyl]amino] propylboronic acid.

6. A compound having the formula (IC)

$$R^{9a}\diagdown\underset{H}{N}\diagdown\underset{\underset{R^{8b}}{|}}{CH}-\underset{\underset{O}{||}}{C}-\underset{H}{N}-\underset{\underset{R^{7b}}{|}}{CH}-\underset{\underset{O}{||}}{C}-\underset{\underset{R^{6}}{|}}{N}-\underset{\underset{R^{5a}}{|}}{CH}-\underset{\underset{O}{||}}{C}-\underset{H}{N}-\underset{\underset{R^{4}}{|}}{CH}-\underset{\underset{O}{||}}{C}-\underset{\underset{R^{3}}{|}}{N}-\underset{\underset{R^{2a}}{|}}{CH}-\underset{\underset{O}{||}}{C}-\underset{H}{N}-\underset{\underset{R^{1}}{|}}{CH}-E$$

wherein

E is —CHO or —B(OH)$_2$;

$R^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

$R^{2a}$ is selected from the group consisting of lower alkyl, hydroxy-lower alkyl, carboxy-lower alkyl, aryl-lower alkyl, aminocarbonyl-lower alkyl and lower cycloalkyl-lower alkyl;

$R^3$ is hydrogen or lower alkyl; or taken together with $R^{2a}$ to form di- or trimethylene optionally substituted by hydroxy;

$R^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

$R^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

$R^6$ is hydrogen or lower alkyl;

$R^{7b}$ is selected from the group consisting of aryl-lower alkylthio-lower alkyl, aryl-lower alkoxy-aryl-lower alkyl, aryl-lower alkoxycarbonyl-lower alkyl, aryl-lower alkylcarbonyl-lower alkyl, nitroguanidino-lower alkyl, arylsulfonyl-guanidino-lower alkyl, lower alkylsulfonyl-lower alkyl, acetamidomethylthio-lower alkyl, aryl and heteroaryl-lower alkyl;

$R^{8b}$ is selected from the group consisting of mercapto-lower alkyl, lower alkylsulfonyl-lower alkyl, aryl-lower alkoxy-lower alkyl and aryl-heteroaryl-lower alkyl;

$R^{9a}$ is selected from the group consisting of lower alkylcarbonyl, carboxy-lower alkyl-carbonyl, arylcarbonyl, lower alkylsulfonyl, arylsulfonyl, lower alkoxycarbonyl and aryl-lower alkoxycarbonyl;

or basic salts of acidic compounds thereof.

7. The compound of claim 6, wherein said compound is selected from the group consisting of:

1(RS)-[[N-[N-[N-[N-[N-Acetyl-1-(2,4-dinitrophenyl)-L-histidyl]-O-benzyl-L-α-glutamyl]-2-methyl-L-phenylalanyl]-3-methyl-L-valyl]-L-leucyl]amino]propylboronic acid;

1(RS)-[[N-[N-[N-[N2-[N-acetyl-1-(2,4-dinitrophenyl)-L-histidyl]-O-benzyl-N6-(p-toluenesulfonyl)-L-arginyl]-2-methyl-L-phenylalanyl]-3-methyl-L-valyl]-L-leucyl]amino]propylboronic acid;

1(RS)-[[N-[N-[N-[N-[N-acetyl-1-(2,4-dinitrophenyl)-L-histidyl]-O-benzyl-D-tyrosyl]-2-methyl-L-phenylalanyl]-3-methyl-L-valyl]-L-leucyl]amino]propylboronic acid;

1(RS)-[[N-[N-[N-[N-[N-acetyl-1-(2,4-dinitrophenyl)-L-histidyl]-4-nitro-D-phenylalanyl]-2-methyl-L-phenylalanyl]-3-methyl-L-valyl]-L-leucyl]amino]propylboronic acid;

1(RS)-[[N-[N-[N-[N-[N-acetyl-1-(2,4-dinitrophenyl)-L-histidyl]-O-benzyl-D-seryl]-2-methyl-L-phenylalanyl]-3-methyl-L-valyl]-L-leucyl]amino]propylboronic acid;

1(RS)-[[N-[N-[N-[N-[N-acetyl-1-(2,4-dinitrophenyl)-L-histidyl]-D-2-phenylglycyl]-2-methyl-L-phenylalanyl]-3-methyl-L-valyl]-L-leucyl]amino]propylboronic acid;

1(RS)-[[N-[N-[N-[N2-[N-acetyl-O-benzyl-L-seryl]-nitro-L-arginyl]-2-methyl-L-phenylalanyl]-3-methyl-L-valyl]-L-leucyl]amino]propylboronic acid;

1(RS)-[[N-[N-[N-[N-[N-acetyl-O-benzyl-L-seryl]-S-benzyl-L-cysteinyl]-2-methyl-L-phenylalanyl]-3-methyl-L-valyl]-L-leucyl]amino]propylboronic acid;

1(RS)-[[N-[N-[N-[N-[N-acetyl-O-benzyl-L-seryl]-D-tryptophyl]-2-methyl-L-phenylalanyl]-3-methyl-L-valyl]-L-leucyl]amino]propylboronic acid;

1(RS)-[[N-[N-[N-[N2-(N-acetyl-S,S-dioxo-L-methionyl]-N6-nitro-L-arginyl]-2-methyl-L-phenylalanyl]-3-methyl-L-valyl]-L-leucyl]amino]propylboronic acid; and 2(RS)-[[N-[N-[N-[N2-(N-acetyl-L-tyrosyl)-N6-nitro-L-arginyl]-2-methyl-L-phenylalanyl]-3-methyl-L-valyl]-L-leucyl]amino]-4,4,4-trifluorobutyraldehyde.

8. A compound having the formula

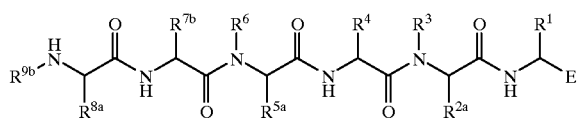

(IF)

wherein

E is —CHO or —B(OH)$_2$;

$R^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

$R^{2a}$ is selected from the group consisting of lower alkyl, hydroxy-lower alkyl, carboxy-lower alkyl, aryl-lower alkyl, aminocarbonyl-lower alkyl and lower cycloalkyl-lower alkyl;

$R^3$ is hydrogen or lower alkyl; or taken together with $R^{2a}$ form di- or trimethylene optionally substituted by hydroxy;

$R^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

$R^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

$R^6$ is hydrogen or lower alkyl;

$R^{7b}$ is selected from the group consisting of aryl-lower alkylthio-lower alkyl, aryl-lower alkoxy-aryl-lower alkyl, aryl-lower alkoxycarbonyl-lower alkyl, aryl-lower alkylcarbonyl-lower alkyl, nitroguanidino-lower alkyl, arylsulfonyl-guanidino-lower alkyl, lower alkylsulfonyl-lower alkyl, acetamidomethylthio-lower alkyl, aryl and heteroaryl-lower alkyl;

$R^{8a}$ is selected from the group consisting of lower alkyl, hydroxy-lower alkyl, carboxy-lower alkyl and aryl-lower alkyl; and $R^{9b}$ is selected from the group consisting of aryl-lower alkylcarbonyl, heteroaryl-lower alkylcarbonyl, arylaminocarbonyl-lower alkylcarbonyl, heteroarylthio-lower alkylcarbonyl, heteroarylcarbonyl, hydroxyfluorenylcarbonyl, heteroarylcarbonyl-lower alkylcarbonyl, lower alkoxy-lower alkylcarbonyl, aryl-carbonyl-lower alkylcarbonyl, lower alkoxy-lower alkoxy-lower alkoxy-lower alkylcarbonyl, arylcarbonylamino-lower alkylcarbonyl, lower cycloalkyl-lower alkylcarbonyl, lower alkylcarbonyl-lower cycloalkyl-lower alkylcarbonyl, lower alkylcarbonylamino-lower alkylcarbonyl, heterocyclylcarbonyl, lower alkylcarbonyloxy-lower alkylcarbonyl, lower alkoxycarbonyl-lower alkylcarbonyl, aryloxy-lower alkylcarbonyl, lower alkynylcarbonyl and lower cycloalkylcarbonyl;

or basic salts of acidic compounds thereof.

9. The compound of claim 8, wherein said compound is selected from the group consisting of:

2(RS)-[[N-[N-[N-[N-[N-[2-(2,4,6-Trimethylphenyl)acetyl]-L-seryl]-O-benzyl-D-seryl]-2-methyl-L- phenylalanyl]-3-methyl-L-valyl]-L-leucyl]amino]-4,4,
4-trifluorobutyraldehyde;

2(RS)-[[N-[N-[N-[N-[N-[(1H-benzotriazol-5-yl)
carbonyl-L-seryl]-O-benzyl-D-seryl]-2-methyl-L-
phenylalanyl]-3-methyl-L-valyl]-L-leucyl]amino]-4,4,
4-trifluorobutyraldehyde;

2(RS)-[[N-[N-[N-[N-[4-(phenylcarbamoyl)-butyryl]-
L-seryl]-O-benzyl-D-seryl]-2-methyl-L-phenylalanyl]-
3-methyl-L-valyl]-L-leucyl]amino]-4,4,4-
trifluorobutyraldehyde;

2(RS)-[N-[N-[N-[N-[N-[2-[(4,6-dimethyl-2-pyrimidinyl)
thio]acetyl]-L-seryl]-O-benzyl-D-seryl]-2-methyl-L-
phenylalanyl]-3-methyl-L-valyl]-L-leucyl ]amino]-4,4,
4-trifluorobutyraldehyde;

2(RS)-[[N-[N-[N-[N-[N-[(2-chloro-3-pyridyl)carbonyl]-
L-seryl]-O-benzyl-D-seryl]-2-methyl-L-phenylalanyl]-
3-methyl-L-valyl]-L-leucyl]amino]-4,4,4-
trifluorobutyraldehyde;

2(RS)-[[N-[N-[N-N-[N-[(9-hydroxy-9-fluorenyl)
carbonyl-L-seryl]-O-benzyl-D-seryl]-2-methyl-L-
phenylalanyl]-3-methyl-L-valyl]-L-leucyl]amino]-4,4,
4-trifluorobutyraldehyde;

2(RS)-[[N-[N-[N-[N-[N-[(2-furoyl)-L-seryl]-O-benzyl-
D-seryl]-2-methyl-L-phenylalanyl]-3-methyl-L-valyl]-
L-leucyl]amino]-4,4,4-trifluorobutyraldehyde;

2(RS)-[[N-[N-[N-[N-[N-[2(RS)-(4-nitrophenyl)
propionyl]-L-seryl]-O-benzyl-D-seryl]-2-methyl-L-
phenylalanyl]-3-methyl-L-valyl]-L-leucyl]amino]-4,4,
4-trifluorobutyraldehyde;

2(RS)-[[N-[N-[N-[N-[N-[2-(2-chlorophenyl)acetyl]-L-
seryl]-O-benzyl-D-seryl]-2-methyl-L-phenylalanyl]-3-
methyl-L-valyl]-L-leucyl]amino]-4,4,4-
trifluorobutyraldehyde;

2(RS)-[[N-[N-[N-[N-[N-(2-ethoxyacetyl)-L-seryl]-O-
benzyl-D-seryl]-2-methyl-L-phenylalanyl]-3-methyl-
L-valyl]-L-leucyl]amino]-4,4,4-
trifluorobutyraldehyde; and 2(RS)-[[N-[N-[N-[N-[N-[(3-fluoro-4-hydroxyphenyl)
acetyl]-L-seryl]-O-benzyl-D-seryl]-2-methyl-L-
phenylalanyl]-3-methyl-L-valyl]-L-leucyl]amino]-4,4,
4-trifluorobutyraldehyde.

10. A compound of the formula

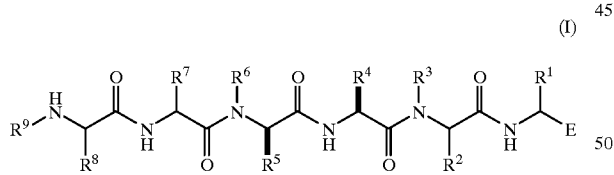

(I)

wherein

E is —CHO or —B(OH)$_2$;

R$^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

R$^2$ is R$^{2a}$ or R$^{2b}$;

R$^{2a}$ is selected from the group consisting of lower alkyl, hydroxy-lower alkyl, carboxy-lower alkyl, aryl-lower alkyl, aminocarbonyl-lower alkyl and lower cycloalkyl-lower alkyl;

R$^{2b}$ is aryl-lower alkoxy-aryl-lower alkyl or heteroaryl-lower alkyl;

R$^3$ is hydrogen or lower alkyl; or taken together with R$^2$ form di- or trimethylene optionally substituted by hydroxy;

R$^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

R$^5$ is R$^{5a}$ or R$^{5b}$;

R$^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

R$^{5b}$ is lower cycloalkyl-lower alkyl;

R$^6$ is hydrogen or lower alkyl;

R$^7$ is selected from the group consisting of nitroguanidino-lower alkyl, lower alkylsulfonyl-lower alkyl and acetamidomethylthio-lower alkyl;

R$^{8a}$ is selected from the group consisting of lower alkyl, hydroxy-lower alkyl, carboxy-lower alkyl and aryl-lower alkyl;

R$^{8b}$ is selected from the group consisting of mercapto-lower alkyl, lower alkylsulfonyl-lower alkyl, aryl-lower alkoxy-lower alkyl and aryl-heteroaryl-lower alkyl;

R$^9$ is R$^{9a}$ or R$^{9b}$;

R$^{9a}$ is selected from the group consisting of lower alkylcarbonyl, carboxy-lower alkyl-carbonyl, arylcarbonyl, lower alkylsulfonyl, arylsulfonyl, lower alkoxycarbonyl and aryl-lower alkoxycarbonyl;

R$^{9b}$ is selected from the group consisting of aryl-lower alkylcarbonyl, heteroaryl-lower alkylcarbonyl, arylaminocarbonyl-lower alkylcarbonyl, heteroarylthio-lower alkylcarbonyl, heteroarylcarbonyl, hydroxyfluorenylcarbonyl, heteroarylcarbonyl-lower alkylcarbonyl, lower alkoxy-lower alkylcarbonyl, aryl-carbonyl-lower alkylcarbonyl, lower alkoxy-lower alkoxy-lower alkoxy-lower alkylcarbonyl, arylcarbonylamino-lower alkylcarbonyl, lower cycloalkyl-lower alkylcarbonyl, lower alkylcarbonyl-lower cycloalkyl-lower alkylcarbonyl, lower alkylcarbonylamino-lower alkylcarbonyl, heterocyclylcarbonyl, lower alkylcarbonyloxy-lower alkylcarbonyl, lower alkoxycarbonyl-lower alkylcarbonyl, aryloxy-lower alkylcarbonyl, lower alkynylcarbonyl and lower cycloalkylcarbonyl;

or basic salts of acidic compounds thereof.

11. A compound of the formula

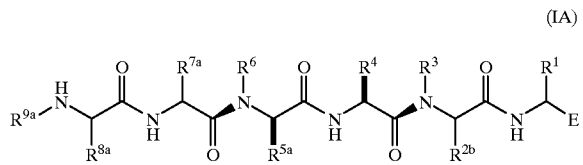

(IA)

wherein

E is —CHO or —B(OH)$_2$;

R$^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

$R^{2b}$ is aryl-lower alkoxy-aryl-lower alkyl or heteroaryl-lower alkyl;

$R^3$ is hydrogen or lower alkyl; or taken together with $R^{2b}$ form di- or trimethylene optionally substituted by hydroxy;

$R^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

$R^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

$R^6$ is hydrogen or lower alkyl;

$R^{7a}$ is carboxy-lower alkyl;

$R^{8a}$ is selected from the group consisting of lower alkyl, hydroxy-lower alkyl, carboxy-lower alkyl and aryl-lower alkyl;

$R^{9a}$ is selected from the group consisting of lower alkylcarbonyl, carboxy-lower alkyl-carbonyl, arylcarbonyl, lower alkylsulfonyl, arylsulfonyl, lower alkoxycarbonyl and aryl-lower alkoxycarbonyl;
or basic salts of acidic compounds thereof.

12. The compound of claim 11, wherein said compound is selected from the group consisting of:

2(RS)-[[N-[N-[N-[N-[N-(3-Carboxypropionyl)-L-α-aspartyl]-L-α-glutamyl]-2-methyl-L,-phenylalanyl]-3-methyl-L-valyl]-O-benzyl-L-tyrosyl]amino]-4,4,4-trifluorobutyraldehyde;

2(RS)-[[N-[N-[N-[N-[N-(3-carboxypropionyl)-L-α-aspartyl]-α-glutamyl]-2-methyl-L-phenylalanyl]-3-methyl-L-valyl]-O-(2,6-dichlorobenzyl)-L-tyrosyl]amino]-4,4,4-trifluorobutyraldehyde; and 2(RS )-[[N-[N-[N-[N-[N-(3-carboxypropionyl)-L-α-aspartyl]-L-α-glutamyl]-2-methyl-L-phenylalanyl]-3-methyl-L-valyl]-2-(3-thienyl)-L-alanyl]amino]-4,4,4-trifluorobutyraldehyde.

13. A compound having the formula

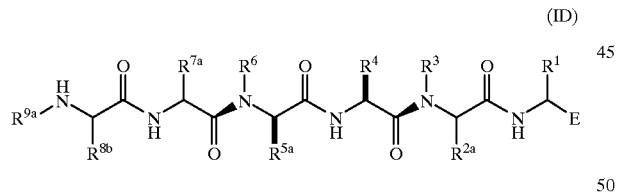

(ID)

wherein

E is —CHO or —B(OH)$_2$;

$R^1$ is selected from the group consisting of lower alkyl, halo-lower alkyl, cyano-lower alkyl, lower-alkylthio-lower alkyl, aryl-lower alkylthio-lower alkyl, aryl-lower alkyl, heteroaryl-lower alkyl, lower alkenyl and lower alkynyl;

$R^{2a}$ is selected from the group consisting of lower alkyl, hydroxy-lower alkyl, carboxy-lower alkyl, aryl-lower alkyl, aminocarbonyl-lower alkyl and lower cycloalkyl-lower alkyl;

$R^3$ is hydrogen or lower alkyl; or taken together with $R^{2a}$ form di- or trimethylene optionally substituted by hydroxy;

$R^4$ is selected from the group consisting of lower alkyl, hydroxy-lower alkyl, lower cyclo-alkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl and lower cycloalkyl;

$R^{5a}$ is selected from the group consisting of lower alkyl, hydroxy-lower alkyl, lower alkylthio-lower alkyl, aryl-lower alkyl, aryl-lower alkylthio-lower alkyl, cyano-lower alkylthio-lower alkyl and lower cycloalkyl;

$R^6$ is hydrogen or lower alkyl;

$R^{7a}$ is selected from the group consisting of isopropyl and cyclohexyl;

$R^{8b}$ is selected from the group consisting of mercapto-lower alkyl, lower alkylsulfonyl-lower alkyl, aryl-lower alkoxy-lower alkyl and aryl-heteroaryl-lower alkyl;

$R^{9a}$ is selected from the group consisting of lower alkylcarbonyl, carboxy-lower alkyl-carbonyl, arylcarbonyl, lower alkylsulfonyl, arylsulfonyl, lower alkoxycarbonyl and aryl-lower alkoxycarbonyl;
or basic salts of acidic compounds thereof.

14. The compound of claim 13, wherein said compound is selected from the group consisting of:

2(RS)-[[N-[N-[-N-[N-[N-(3-Carboxypropionyl)-S,S-dioxo-L-methionyl]-D-valyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-S,S-dioxo-S-methyl-L-cysteinyl]-D-valyl]-2-methyl-L-phenylalanyl]-3-methyl-L-valyl ]-L-leucyl]amino]-4,4,4-trifluorobutyraldehyde;

2(RS)-[[N-[N-[N-[N-[N-(3-carboxypropionyl)-1-(2,4-dinitrophenyl)-L-histidyl]-D-valyl]-2-methyl-L-phenylalanyl]-3-methyl-L-valyl]-L-leucyl]amino]-4,4,4-trifluorobutyraldehyde;

2(RS )-[[N-[N-[-[N-[N-(3-carboxypropionyl)-L-cysteinyl]-D-valyl]-2-methyl-L-phenylalanyl]-3-methyl-L-valyl]-L-leucyl]amino]-4,4,4-trifluorobutyraldehyde; and 1(RS)-[[N-[N-[N-[N-acetyl-1-(2,4-dinitrophenyl)-L-histidyl]-L-2-cyclohexylglycyl]-2-methyl-L-phenylalanyl]-3-methyl-L-valyl]-L-leucyl]amino] propylboronic acid.

15. The compound selected from the group consisting of:

2(RS)-[[N-[N-[N-[N-[N-[4-(4-Methylphenyl)butyryl]-L-α-aspartyl]-L-(α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-[3-(4-methylbenzoyl) propionyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[-[N-[N-[N-[N-[2-[2-(2-methoxyethoxy) ethoxyacetyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[2-(4-oxo-2-thioxo-3-thiazolidinyl) acetyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-[3-(2-methyl-4-nitro-1-imidazolyl)propionyl]-L-α-aspartyl]-L-α-glutamyl]-2-methyl-L-phenylalanyl]-3-methyl-L-valyl]-L-leucyl] amino]-4,4,4-trifluorobutyraldehyde;

2(RS)-[[N-[N-[N-[N-[N-(5-hexynoyl)-L-α-aspartyl]-L-(α-glutamyl]-2-methyl-L-phenylalanyl]-3-methyl-L-valyl]-L-leucyl]amino]-4,4,4-trifluorobutyraldehyde;

2(RS)-[[N-[N-[-[N-[-N-[N-(6-quinolyl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[-N-[N-[-[N -[N-(6-oxo-3-pyranyl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-[2-(1,3-benzodioxol-5-yl)acetyl]-L-α-aspartyl]-α-glutamyl]-2-methyl-L-phenylalanyl]-3-methyl-L-valyl]-L-leucyl]amino]-4,4,4-trifluorobutyraldehyde;

2(RS)-[[N-[N-[N-[-N[N-[(5,6-dihydro-6,6-dimethyl-4-oxo-4H-pyran-2-yl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-[2-(2-naphthyl)acetyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-benzamidopropionyl)-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-[(1,2,3,4-tetrahydro-2,4-dioxo-5-pyrimidinyl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-methyl-2-thenoyl)-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-(2-cyclohexyacetyl)-L-α-aspartyl]-L-α-glutamyl]-2-methyl-L-phenylalanyl]-3-methyl-L-valyl]-L-leucyl]amino]-4,4,4-trifluorobutyraldehyde;

2(RS)-[[N-[N-[N-[N-[N-[2(RS)-(4-nitrophenyl)propionyl]-L-α-aspartyl]-L-α-glutamyl]-2-methyl-L-phenylalanyl]-3-methyl-L-valyl]-L-leucyl]amino]-4,4,4-trifluorobutyraldehyde;

1(RS)-[[N-[N-[N-[N-[N-[(6-oxo-6H-pyran-3-yl)carbonyl]-L-α-aspartyl]-L-α-glutamyl]-2-methyl-L-phenylalanyl]-3-methyl-L-valyl]-L-leucyl]amino]propylboronic acid;

1(RS)-[[N-[N-[N-[N-[N-(4-acetamidobutyryl)-L-α-aspartyl]-L-α-glutamyl]-2-methyl-L-phenylalanyl]-3-methyl-L-valyl]-L-leucyl]amino]propylboronic acid; and 1(RS)-[[N-[N-[N-[N-[N-(2-acetoxyacetyl)-L-α-aspartyl]-L-α-glutamyl]-2-methyl-L-phenylalanyl]-3-methyl-L-valyl]-L-leucyl]amino]propylboronic acid.

* * * * *

UNITED STATES PATENT AND TRADEMARK OFFICE
CERTIFICATE OF CORRECTION

PATENT NO.   : 6,372,883 B1                                                       Page 1 of 1
DATED        : April 16, 2002
INVENTOR(S)  : Attwood et al.

It is certified that error appears in the above-identified patent and that said Letters Patent is hereby corrected as shown below:

Column 67,
Lines 33-37, please delete:
"2(RS)-[[N-[N-[N-[N-[N-(3-carboxypropionyl)-L-α-aspartyl]-α-glutamyl]-2-methyl-L-phenylalanyl]-3-methyl-L-valyl]-O-(2,6-dichlorobenzyl)-L-tyrosyl]amino]-4,4,4-trifluorobutyraldehyde; and" and insert therefore:
-- 2(RS)-[[N-[N-[N-[N-[N-(3-carboxypropionyl)-L-α-aspartyl]-L-α-glutamyl]-2-methyl-L-phenylalanyl]-3-methyl-L-valyl]-O-(2,6-dichlorobenzyl)-L-tyrosyl]amino]-4,4,4-trifluorobutyraldehyde; and --

Column 69,
Lines 9-16, please delete:
"2(RS)-[[N-[N-[N-[N-[N-[2-(1,3-benzodioxol-5-yl)acetyl]-L-α-aspartyl]-α-glutamyl]-2-methyl-L-phenylalanyl]-3-methyl-L-valyl]-L-leucyl]amino]-4,4,4-trifluorobutyraldehyde;
2(RS)-[[N-[N-[N-[-[N[N[(5,6-dihydro-6,6-dimethyl-4-oxo-4H-pyran-2-yl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde;" and insert therefore:
-- 2(RS)-[[N-[N-[N-[N-[N-[2-(1,3-benzodioxol-5-yl)acetyl]-L-α-aspartyl]-L-α-glutamyl]-2-methyl-L-phenylalanyl]-3-methyl-L-valyl]-L-leucyl]amino]-4,4,4-trifluorobutyraldehyde;
2(RS)-[[N-[N-[N-[N-[N-[(5,6-dihydro-6,6-dimethyl-4-oxo-4H-pyran-2-yl)carbonyl]-L-α-aspartyl]-L-α-glutamyl]-2-methyl-L-phenylalanyl]-3-methyl-L-valyl]-L-leucyl]amino]-4,4,4-trifluorobutyraldehyde; --

Signed and Sealed this

Twenty-second Day of October, 2002

*Attest:*

JAMES E. ROGAN
*Attesting Officer*         *Director of the United States Patent and Trademark Office*

```
                          SEQUENCE LISTING

<160> NUMBER OF SEQ ID NOS: 24

<210> SEQ ID NO 1
<211> LENGTH: 7475
<212> TYPE: DNA
<213> ORGANISM: Artificial Sequence
<220> FEATURE:
<223> OTHER INFORMATION: Description of Artificial Sequence: Vector and
      Gene Fragments

<400> SEQUENCE: 1
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta aatctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg gcgcccaata   1080
cgcaaaccgc ctctccccgc gcgttggccg attcattaat gcagctggca cgacaggttt   1140
cccgactgga aagcgggcag tgagcgcaac gcaattaatg tgagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
```

-continued

```
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga aacagccagt ccgtttaggt gttttcacga    1500
gcacttcacc aacaaggacc atagattatg aaaactgaag aaggtaaaact ggtaatctgg    1560 attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt tggtggctac    1740
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta taacaaagat ctgctgccga acccgccaaa aacctgggaa    1920
gagatcccgg cgctggataa agaactgaaa gcgaaaggta gagcgcgct gatgttcaac    1980 ctgcaagaac cgtacttcac ctggccgctg attgctgctg acggggtta tgcgttcaag    2040 tatgaaaacg gcaagtacga cattaaagac gtgggcgtgg ataacgctgg cgcgaaagcg    2100
ggtctgacct cctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta taaagacaa accgctgggt gccgtagcgc tgaagtctta cgaggaagag    2460
ttggcgaaag atccacgtat tgccgccacc atggaaaacg cccagaaagg tgaaatcatg    2520
ccgaacatcc gcagatgtc cgctttctgg tatgccgtgc gtactgcggt gatcaacgcc    2580
gccagcggtc gtcagactgt cgatgaagcc ctgaaagacg cgcagactaa ttcgagctcg    2640
aacaacaaca acaataacaa taacaacaac ctcgggatcg agggaaggat ttcagaattc    2700
atggggaggg agatacatct gggaccggca gacagccttg aagggcaggg gtggcgactc    2760
ctcgcgcata ttacggccta ctctcaacag acgcggggcc tacttggctg catcatcact    2820
agcctcacag gccgggacag gaaccaggtc gagggggagg tccaaatggt ctccaccgca    2880
acacaatctt tcctggcgac ctgcgtcaat ggcgtgtgtt ggactgtcta tcatggtgcc    2940
ggctcaaaga cccttgccgg cccaaagggc ccaatcaccc aaatgtacac caatgtggac    3000
caggacctcg tcggctggca agcgcccccc ggggcgcgct ccttgacacc atgcacctgc    3060
ggcagctcag acctttactt ggtcacgagg catgccgatg tcattccggt gcgccggcgg    3120
ggcgacagca ggggaagcct actctccccc aggcccgtct cctacttgaa gggctcttcg    3180
ggcggtccac tgctctgccc ctcggggcac gctgtgggca tcttccgggc tgccgtgtgc    3240
acccgagggg ttgcgaaggc ggtggacttt gtacccgtcg agtctatgga aaccactatg    3300
cggtccccgg tcttcacgga caactcgtcc cctccggccg tatgcatggg aggaggagga    3360
ggaggaggag gaggaggagg aggatccatg agcacctggg tgctagtagg cggagtccta    3420
gcagctctgg ccgcgtattg cctgacaaca ggcagcgtgg tcattgtggg caggatcgtc    3480
ttgtccggaa agccggccat cattcccgac agggaagtcc tctaccggga gttcgatgag    3540
atggaagagt gctagaagct tggcactggc cgtcgtttta caacgtcgtg actgggaaaa    3600
ccctggcgtt acccaactta atcgccttgc agcacatccc cctttcgcca gctggcgtaa    3660
```

-continued

```
tagcgaagag gcccgcaccg atcgcccttc ccaacagttg cgcagcctga atggcgaatg    3720
gcagcttggc tgttttggcg gatgagataa gattttcagc ctgatacaga ttaaatcaga    3780
acgcagaagc ggtctgataa aacagaattt gcctggcggc agtagcgcgg tggtcccacc    3840
tgaccccatg ccgaactcag aagtgaaacg ccgtagcgcc gatggtagtg tggggtctcc    3900
ccatgcgaga gtagggaact gccaggcatc aaataaaacg aaaggctcag tcgaaagact    3960
gggcctttcg ttttatctgt tgtttgtcgg tgaacgctct cctgagtagg acaaatccgc    4020
cgggagcgga tttgaacgtt gcgaagcaac ggcccgagg tggcgggca ggacgcccgc     4080
cataaactgc caggcatcaa attaagcaga aggccatcct gacggatggc cttttgcgt     4140
ttctacaaac tcttttgtt tattttttcta aatacattca aatatgtatc cgctcatgag    4200
acaataaccc tgataaatgc ttcaataata ttgaaaaagg aagagtatga gtattcaaca    4260
tttccgtgtc gcccttattc cctttttttgc ggcattttgc cttcctgttt ttgctcaccc    4320
agaaacgctg gtgaaagtaa aagatgctga agatcagttg ggtgcacgag tgggttacat    4380
cgaactggat ctcaacagcg gtaagatcct tgagagtttt cgccccgaag aacgttctcc    4440
aatgatgagc acttttaaag ttctgctatg tggcgcggta ttatcccgtg ttgacgccgg    4500
gcaagagcaa ctcggtcgcc gcatacacta ttctcagaat gacttggttg agtactcacc    4560
agtcacagaa aagcatctta cggatggcat gacagtaaga gaattatgca gtgctgccat    4620
aaccatgagt gataacactg cggccaactt acttctgaca acgatcggag gaccgaagga    4680
gctaaccgct tttttgcaca acatggggga tcatgtaact cgccttgatc gttgggaacc    4740
ggagctgaat gaagccatac caaacgacga gcgtgacacc acgatgcctg tagcaatggc    4800
aacaacgttg cgcaaactat taactggcga actacttact ctagcttccc ggcaacaatt    4860
aatagactgg atggaggcgg ataaagttgc aggaccactt ctgcgctcgg cccttccggc    4920
tggctggttt attgctgata atctggagc cggtgagcgt gggtctcgcg gtatcattgc      4980
agcactgggg ccagatggta agccctcccg tatcgtagtt atctacacga cggggagtca    5040
ggcaactatg gatgaacgaa atagacagat cgctgagata ggtgcctcac tgattaagca    5100
ttggtaactg tcagaccaag tttactcata tatactttag attgatttac cccggttgat    5160
aatcagaaaa gccccaaaaa caggaagatt gtataagcaa atatttaaat tgtaaacgtt    5220
aatattttgt taaaattcgc gttaaatttt tgttaaatca gctcattttt taaccaatag    5280
gccgaaatcg gcaaaatccc ttataaatca aagaatagcc cgagatagg gttgagtgtt    5340
gttccagttt ggaacaagag tccactatta agaacgtgg actccaacgt caaagggcga     5400
aaaaccgtct atcagggcga tggcccacta cgtgaaccat cacccaaatc aagttttttg    5460
gggtcgaggt gccgtaaagc actaaatcgg aaccctaaag ggagccccg atttagagct     5520
tgacggggaa agccggcgaa cgtggcgaga aggaaggga agaaagcgaa aggagcgggc     5580
gctagggcgc tggcaagtgt agcggtcacg ctgcgcgtaa ccaccacacc cgccgcgctt    5640
aatgcgccgc tacagggcgc gtaaaaggat ctaggtgaag atcctttttg ataatctcat    5700
gaccaaaatc ccttaacgtg agttttcgtt ccactgagcg tcagacccg tagaaaagat     5760
caaaggatct tcttgagatc cttttttttct gcgcgtaatc tgctgcttgc aaacaaaaaa    5820
accaccgcta ccagcggtgg tttgtttgcc ggatcaagag ctaccaactc ttttttccgaa    5880
ggtaactggc ttcagcagag cgcagatacc aaatactgtc cttctagtgt agccgtagtt    5940
aggccaccac ttcaagaact ctgtagcacc gcctacatac ctcgctctgc taatcctgtt    6000
accagtggct gctgccagtg gcgataagtc gtgtcttacc gggttggact caagacgata    6060
```

-continued

```
gttaccggat aaggcgcagc ggtcgggctg aacgggggt tcgtgcacac agcccagctt      6120
ggagcgaacg acctacaccg aactgagata cctacagcgt gagctatgag aaagcgccac      6180
gcttcccgaa gggagaaagg cggacaggta tccggtaagc ggcagggtcg aacaggaga      6240 gcgcacgagg gagcttccag ggggaaacgc ctggtatctt tatagtcctg tcgggtttcg      6300
ccacctctga cttgagcgtc gattttttgtg atgctcgtca gggggcgga gcctatggaa      6360 aaacgccagc aacgcggcct ttttacggtt cctggccttt tgctggcctt ttgctcacat      6420
gttctttcct gcgttatccc ctgattctgt ggataaccgt attaccgcct ttgagtgagc      6480
tgataccgct cgccgcagcc gaacgaccga gcgcagcgag tcagtgagcg aggaagcgga      6540
agagcgcctg atgcggtatt ttctccttac gcatctgtgc ggtatttcac accgcatatg      6600
gtgcactctc agtacaatct gctctgatgc cgcatagtta agccagtata cactccgcta      6660
tcgctacgtg actgggtcat ggctgcgccc cgacacccgc caacacccgc tgacgcgccc      6720
tgacgggctt gtctgctccc ggcatccgct tacagacaag ctgtgaccgt ctccgggagc      6780
tgcatgtgtc agaggttttc accgtcatca ccgaaacgcg cgaggcagct gcggtaaagc      6840
tcatcagcgt ggtcgtgcag cgattcacag atgtctgcct gttcatccgc gtccagctcg      6900
ttgagtttct ccagaagcgt taatgtctgg cttctgataa agcgggccat gttaagggcg      6960
gttttttcct gtttggtcac ttgatgcctc cgtgtaaggg ggaatttctg ttcatggggg      7020
taatgatacc gatgaaacga gagaggatgc tcacgatacg ggttactgat gatgaacatg      7080
cccggttact ggaacgttgt gagggtaaac aactggcggt atggatgcgg cgggaccaga      7140
gaaaaatcac tcagggtcaa tgccagcgct tcgttaatac agatgtaggt gttccacagg      7200
gtagccagca gcatcctgcg atgcagatcc ggaacataat ggtgcagggc gctgacttcc      7260
gcgtttccag actttacgaa acacggaaac cgaagaccat tcatgttgtt gctcaggtcg      7320
cagacgtttt gcagcagcag tcgcttcacg ttcgctcgcg tatcggtgat tcattctgct      7380
aaccagtaag gcaaccccgc cagcctagcc gggtcctcaa cgacaggagc acgatcatgc      7440
gcacccgtgg ccaggaccca acgctgcccg aaatt                                7475
```

<210> SEQ ID NO 2
<211> LENGTH: 675
<212> TYPE: PRT
<213> ORGANISM: Artificial Sequence
<220> FEATURE:
<223> OTHER INFORMATION: Description of Artificial Sequence: Vector and
      Gene Fragments

<400> SEQUENCE: 2

```
Met Lys Thr Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
    65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
```

-continued

```
                100              105             110
Ala Leu Ser Leu Ile Tyr Asn Lys Asp Leu Pro Asn Pro Pro Lys
            115             120             125
Thr Trp Glu Glu Ile Pro Ala Leu Asp Lys Glu Leu Lys Ala Lys Gly
130             135             140
Lys Ser Ala Leu Met Phe Asn Leu Gln Glu Pro Tyr Phe Thr Trp Pro
145             150             155             160
Leu Ile Ala Ala Asp Gly Gly Tyr Ala Phe Lys Tyr Glu Asn Gly Lys
            165             170             175
Tyr Asp Ile Lys Asp Val Gly Val Asp Asn Ala Gly Ala Lys Ala Gly
            180             185             190
Leu Thr Phe Leu Val Asp Leu Ile Lys Asn Lys His Met Asn Ala Asp
            195             200             205
Thr Asp Tyr Ser Ile Ala Glu Ala Ala Phe Asn Lys Gly Glu Thr Ala
            210             215             220
Met Thr Ile Asn Gly Pro Trp Ala Trp Ser Asn Ile Asp Thr Ser Lys
225             230             235             240
Val Asn Tyr Gly Val Thr Val Leu Pro Thr Phe Lys Gly Gln Pro Ser
            245             250             255
Lys Pro Phe Val Gly Val Leu Ser Ala Gly Ile Asn Ala Ala Ser Pro
            260             265             270
Asn Lys Glu Leu Ala Lys Glu Phe Leu Glu Asn Tyr Leu Leu Thr Asp
            275             280             285
Glu Gly Leu Glu Ala Val Asn Lys Asp Lys Pro Leu Gly Ala Val Ala
            290             295             300
Leu Lys Ser Tyr Glu Glu Glu Leu Ala Lys Asp Pro Arg Ile Ala Ala
305             310             315             320
Thr Met Glu Asn Ala Gln Lys Gly Glu Ile Met Pro Asn Ile Pro Gln
            325             330             335
Met Ser Ala Phe Trp Tyr Ala Val Arg Thr Ala Val Ile Asn Ala Ala
            340             345             350
Ser Gly Arg Gln Thr Val Asp Glu Ala Leu Lys Asp Ala Gln Thr Asn
            355             360             365
Ser Ser Ser Asn Asn Asn Asn Asn Asn Asn Asn Asn Leu Gly Ile
            370             375             380
Glu Gly Arg Ile Ser Glu Phe Met Gly Arg Glu Ile His Leu Gly Pro
385             390             395             400
Ala Asp Ser Leu Glu Gly Gln Gly Trp Arg Leu Leu Ala His Ile Thr
            405             410             415
Ala Tyr Ser Gln Gln Thr Arg Gly Leu Leu Gly Cys Ile Ile Thr Ser
            420             425             430
Leu Thr Gly Arg Asp Arg Asn Gln Val Glu Gly Glu Val Gln Met Val
            435             440             445
Ser Thr Ala Thr Gln Ser Phe Leu Ala Thr Cys Val Asn Gly Val Cys
            450             455             460
Trp Thr Val Tyr His Gly Ala Gly Ser Lys Thr Leu Ala Gly Pro Lys
465             470             475             480
Gly Pro Ile Thr Gln Met Tyr Thr Asn Val Asp Gln Asp Leu Val Gly
            485             490             495
Trp Gln Ala Pro Pro Gly Ala Arg Ser Leu Thr Pro Cys Thr Cys Gly
            500             505             510
Ser Ser Asp Leu Tyr Leu Val Thr Arg His Ala Asp Val Ile Pro Val
            515             520             525
```

```
Arg Arg Arg Gly Asp Ser Arg Gly Ser Leu Leu Ser Pro Arg Pro Val
    530                 535                 540

Ser Tyr Leu Lys Gly Ser Ser Gly Gly Pro Leu Leu Cys Pro Ser Gly
545                 550                 555                 560

His Ala Val Gly Ile Phe Arg Ala Ala Val Cys Thr Arg Gly Val Ala
                565                 570                 575

Lys Ala Val Asp Phe Val Pro Val Glu Ser Met Glu Thr Thr Met Arg
            580                 585                 590

Ser Pro Val Phe Thr Asp Asn Ser Ser Pro Pro Ala Val Cys Met Gly
        595                 600                 605

Gly Gly Gly Gly Gly Gly Gly Gly Gly Ser Met Ser Thr Trp
    610                 615                 620

Val Leu Val Gly Gly Val Leu Ala Ala Leu Ala Ala Tyr Cys Leu Thr
625                 630                 635                 640

Thr Gly Ser Val Val Ile Val Gly Arg Ile Val Leu Ser Gly Lys Pro
                645                 650                 655

Ala Ile Ile Pro Asp Arg Glu Val Leu Tyr Arg Glu Phe Asp Glu Met
            660                 665                 670

Glu Glu Cys
        675

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (3)..(4)
<223> OTHER INFORMATION: METHYLATION
<221> NAME/KEY: MOD_RES
<222> LOCATION: (1)
<223> OTHER INFORMATION: ACETYLATION

<400> SEQUENCE: 3

Asp Xaa Phe Val Leu
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (1)
<223> OTHER INFORMATION: ACETYLATION
<221> NAME/KEY: MOD_RES
<222> LOCATION: (3)..(4)
<223> OTHER INFORMATION: METHYLATION

<400> SEQUENCE: 4

Asp Xaa Phe Val Leu
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: synthesized
      material
```

```
<221> NAME/KEY: MOD_RES
<222> LOCATION: (3)..(4)
<223> OTHER INFORMATION: METHYLATION
<221> NAME/KEY: MOD_RES
<222> LOCATION: (1)
<223> OTHER INFORMATION: ACETYLATION

<400> SEQUENCE: 5

Tyr Xaa Phe Val Leu
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (3)..(4)
<223> OTHER INFORMATION: METHYLATION
<221> NAME/KEY: MOD_RES
<222> LOCATION: (1)
<223> OTHER INFORMATION: ACETYLATION

<400> SEQUENCE: 6

Xaa Glu Phe Val Leu
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (3)..(4)
<223> OTHER INFORMATION: METHYLATION

<400> SEQUENCE: 7

Xaa Glu Phe Val Leu
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (3)..(4)
<223> OTHER INFORMATION: METHYLATION

<400> SEQUENCE: 8

Xaa Glu Phe Val Leu
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (3)..(4)
<223> OTHER INFORMATION: METHYLATION

<400> SEQUENCE: 9
```

Xaa Glu Phe Val Leu
 1               5

<210> SEQ ID NO 10
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 10

Xaa Glu Phe Val Leu
 1               5

<210> SEQ ID NO 11
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 11

Xaa Glu Phe Val Leu
 1               5

<210> SEQ ID NO 12
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 12

Xaa Glu Phe Val Leu
 1               5

<210> SEQ ID NO 13
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 13

Xaa Glu Phe Val Leu
 1               5

<210> SEQ ID NO 14
<211> LENGTH: 5
<212> TYPE: PRT
<213> ORGANISM: Artificial Sequence
<220> FEATURE:
<221> NAME/KEY: MOD_RES

```
<222> LOCATION: (3)..(4)
<223> OTHER INFORMATION: METHYLATION
<223> OTHER INFORMATION: Description of Artificial Sequence: synthesized
      material

<400> SEQUENCE: 14

Xaa Glu Phe Val Leu
 1               5

<210> SEQ ID NO 15
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 15

Xaa Glu Phe Val Leu
 1               5

<210> SEQ ID NO 16
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 16

Xaa Glu Phe Val Leu
 1               5

<210> SEQ ID NO 17
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 17

Xaa Glu Phe Val Leu
 1               5

<210> SEQ ID NO 18
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 18

Xaa Glu Phe Val Leu
 1               5
```

```
<210> SEQ ID NO 19
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 19

Xaa Glu Phe Val Leu
 1               5

<210> SEQ ID NO 20
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 20

Xaa Glu Phe Val Leu
 1               5

<210> SEQ ID NO 21
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 21

Xaa Glu Phe Val Leu
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (3)..(4)
<223> OTHER INFORMATION: METHYLATION

<400> SEQUENCE: 22

Xaa Glu Phe Val Leu
 1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: synthesized
      material
<221> NAME/KEY: MOD_RES
<222> LOCATION: (3)..(4)
<223> OTHER INFORMATION: METHYLATION
```

```
<400> SEQUENCE: 23

Xaa Glu Phe Val Leu
 1               5

<210> SEQ ID NO 24
<211> LENGTH: 5
<212> TYPE: PRT
<213> ORGANISM: Artificial Sequence
<220> FEATURE:
<221> NAME/KEY: MOD_RES
<222> LOCATION: (3)..(4)
<223> OTHER INFORMATION: METHYLATION
<223> OTHER INFORMATION: Description of Artificial Sequence: synthesized
      material

<400> SEQUENCE: 24

Xaa Glu Phe Val Leu
 1               5
```